(12) United States Patent
Meijler et al.

(10) Patent No.: US 9,242,951 B2
(45) Date of Patent: Jan. 26, 2016

(54) COVALENT INHIBITION OF BACTERIAL QUORUM SENSING

(71) Applicant: The National Institute for Biotechnology in the Negev Ltd., Beersheba (IL)

(72) Inventors: Michael M. Meijler, Omer (IL); Josep Rayo, Beersheba (IL); Neri Amara, Beersheba (IL)

(73) Assignee: THE NATIONAL INSTITUTE FOR BIOTECHNOLOGY IN THE NEGEV LTD., Beer-Sheva (IL)

( * ) Notice: Subject to any disclaimer, the term of this patent is extended or adjusted under 35 U.S.C. 154(b) by 0 days.

(21) Appl. No.: 13/927,162

(22) Filed: Jun. 26, 2013

(65) Prior Publication Data

US 2014/0073690 A1   Mar. 13, 2014

Related U.S. Application Data

(63) Continuation of application No. 13/381,952, filed as application No. PCT/IB2010/053061 on Jul. 4, 2010, now Pat. No. 8,501,969.

(60) Provisional application No. 61/222,944, filed on Jul. 3, 2009.

(51) Int. Cl.
C07D 307/00 (2006.01)
C07D 307/33 (2006.01)
C07D 307/32 (2006.01)
C07D 405/12 (2006.01)
C07D 407/12 (2006.01)
A01N 43/08 (2006.01)
A61K 31/365 (2006.01)
A61K 45/06 (2006.01)

(52) U.S. Cl.
CPC .............. *C07D 307/33* (2013.01); *A01N 43/08* (2013.01); *A61K 31/365* (2013.01); *A61K 45/06* (2013.01); *C07D 307/32* (2013.01); *C07D 405/12* (2013.01); *C07D 407/12* (2013.01)

(58) Field of Classification Search
CPC .................................................... C07D 307/33
USPC ......................................................... 549/321
See application file for complete search history.

(56) References Cited

U.S. PATENT DOCUMENTS 7,642,285 B2    1/2010    Blackwell et al.

FOREIGN PATENT DOCUMENTS

| WO | WO0174801    | 10/2001 |
| WO | WO03004017   | 1/2003  |
| WO | WO03022828   | 3/2003  |
| WO | WO03026641   | 4/2003  |
| WO | WO2004016213 | 2/2004  |

OTHER PUBLICATIONS

Mattmann et al. J. Org. Chem. 2010, 75, 6737-6746.*
Amara et al. Journal of the American Chemical Society (2009), 131(30), 10610-10619.*

(Continued)

*Primary Examiner* — Nizal Chandrakumar
(74) *Attorney, Agent, or Firm* — Nixon & Vanderhye P.C.

(57) ABSTRACT

Inhibitors of bacterial communication, such as quorum sensing, and method of use and manufacture thereof.

6 Claims, 19 Drawing Sheets

(56) References Cited

OTHER PUBLICATIONS

Dorwald F. A. Side Reactions in Organic Synthesis, 2005, Wiley: VCH, Weinheim p. IX of Preface p. 1-15.*

Venkatesh et al., J. Pharm. Sci. 89, 145-54 (2000) (p. 146, left column).*

Ner et al. Journal of the American Chemical Society (2009), 131(30), 10610-10619.*

International Search Report for corresponding PCT/IB2010/053061 dated Nov. 19, 2010.

Spandl Richard J et al, Synthesis of a Biotin-Labeled Quorum-Sensing Molecule: Towards a General Method for Target Identification; Synlett (2008), vol. 14, pp. 2122-2126.

Horikawa Manabu et al, Synthesis of Pseudomonas quorum-sensing autoinducer analogs an structural entities required for induction of apoptosis in macrophages; Bioorganic & Medical Chemistry Letters (2006), vol. 16, No. 8, pp. 2130-2133.

Kaufman Gunnar F et al, Antibody Interference with N-Acyl Homoserine Lactone-Mediated Bacterial Quorum Sensing; Journal of American Chemical Society (2006), vol. 128, No. 9, pp. 2802-2803.

Chhabra Siri Ram et al, Synthetic Analogues of the Bacterial Signal (Quorom Sensing) Module N-(3-Oxododecanoyl)-I-homoserine Lactone as Immune Modulators; Journal of Medicinal Chemistry (2003) vol. 46, No. 1, pp. 97-104.

Reverchon Sylvie et al, New synthetic analogues of N-acyl homoserine lactones as agonists or antagonists of transcriptional regulators involved in bacterial quorum sensing; Bioorganic & Medicinal Chemistry Letters (2002), vol. 12, No. 8, pp. 1153-1158.

Amara, Neri et al, Covalent Inhibition of Bacterial Quorum Sensing; Journal of American Chemical Society (2009), vol. 131, No. 30, pp. 10610-10619.

Dubinsky Luba et al, Synthesis and validation of a probe to identify quorum sensing receptors; Chemical Communications (2009), vol. 47, pp. 7378-7380.

Office action for corresponding CN application 201080038367.2, mailed Oct. 10, 2013 (translation only).

Office action for corresponding CN application 201080038367.2, mailed Feb. 14, 2014 (translation and original).

* cited by examiner

Figure 3D1
¹H-NMR for compound 7a:
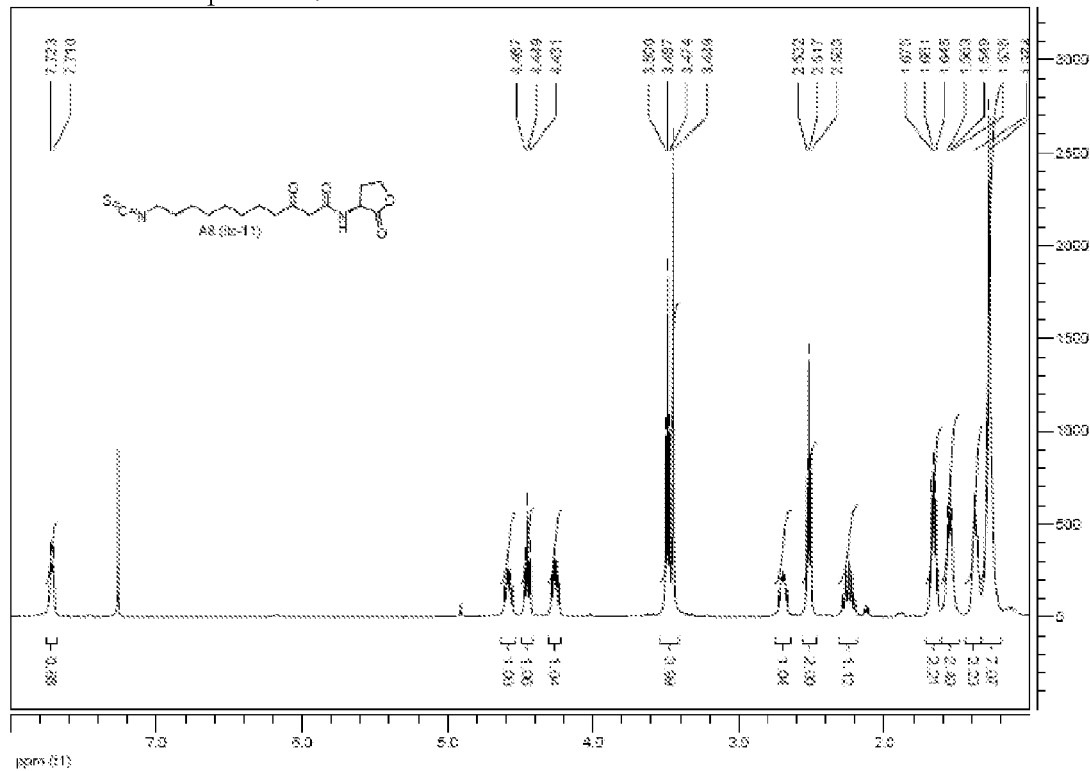

Figure 3D2
$^{13}$C-NMR for compound 7a:
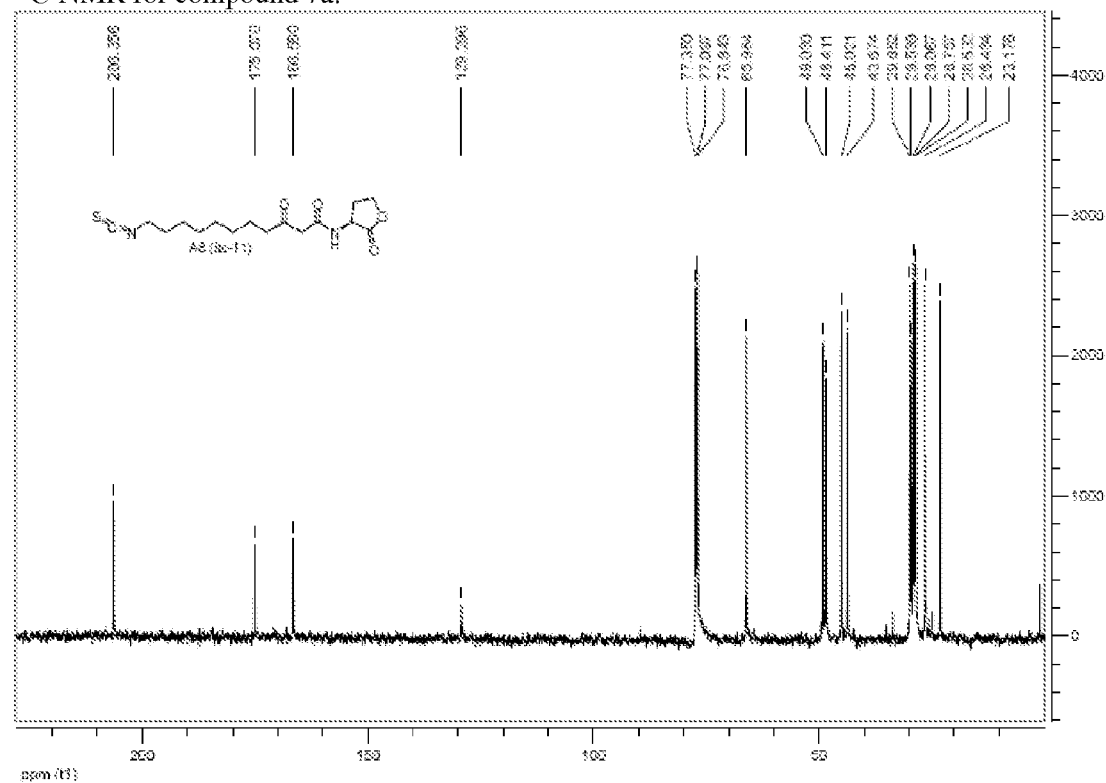

Figure 3E1
¹H-NMR for compound 7b:
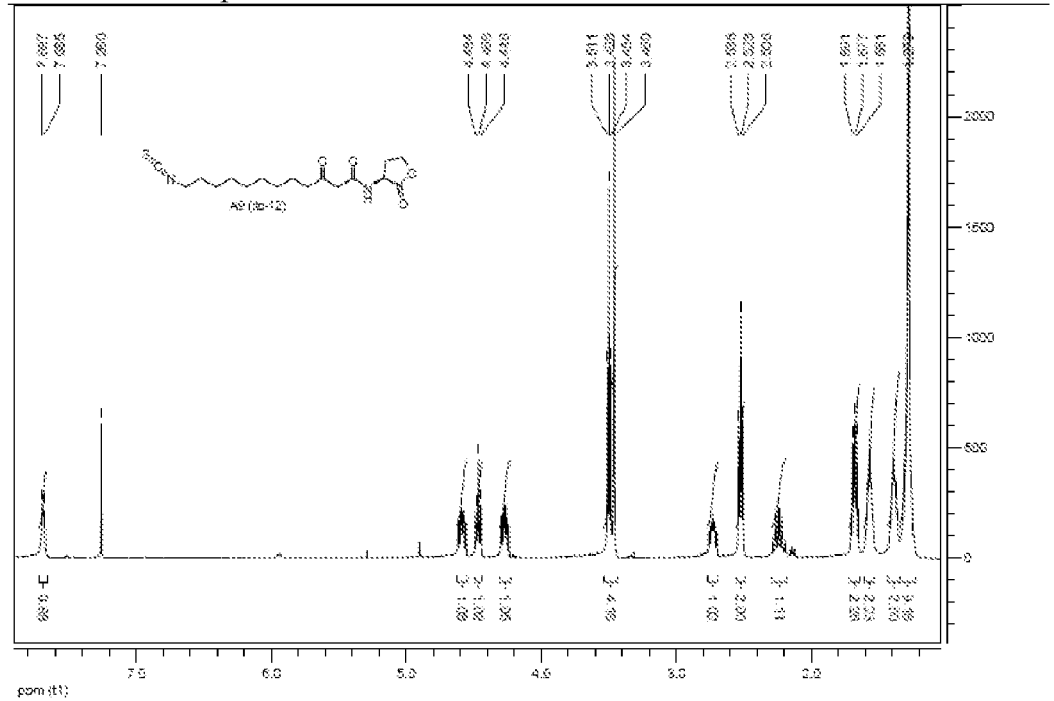

Figure 3E2
$^{13}$C-NMR for compound 7b:
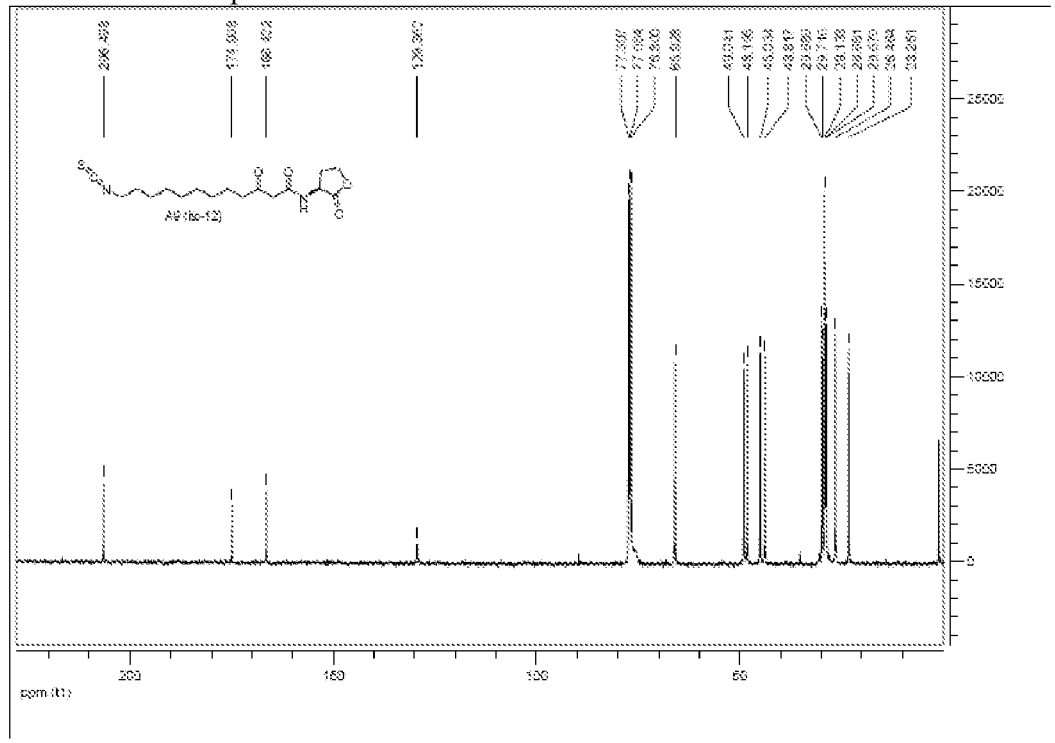

Figure 3F1
¹H-NMR for compound 7c:
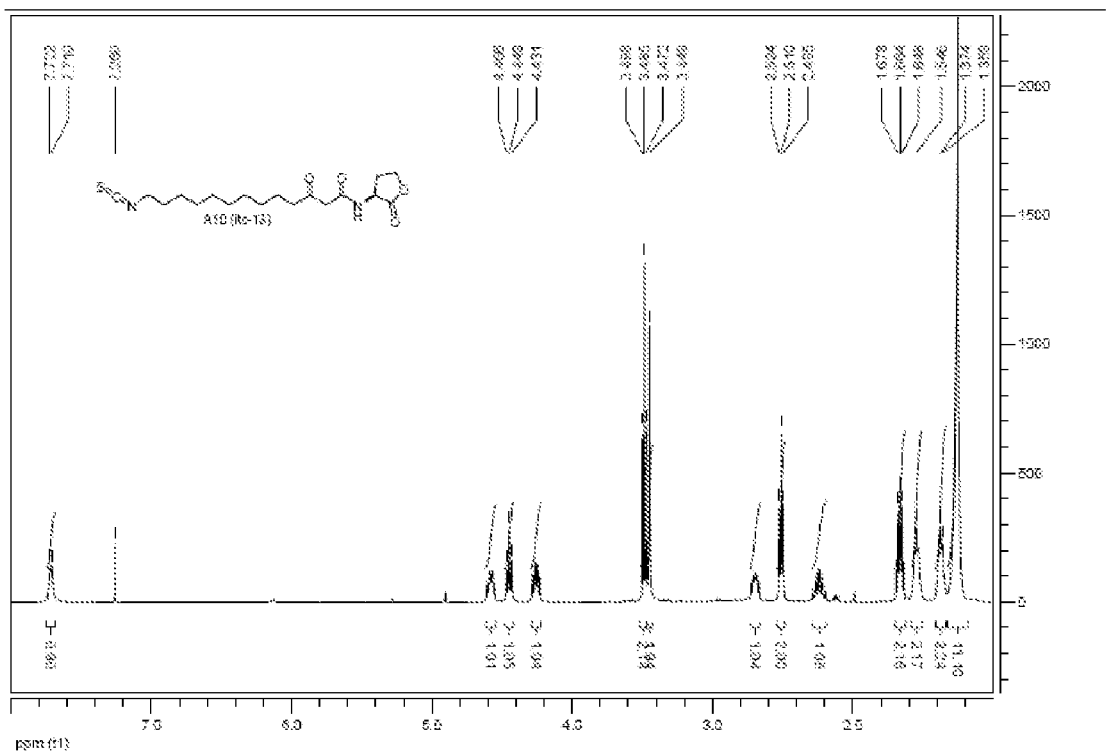

Figure 3F2
$^{13}$C-NMR for compound 7c:
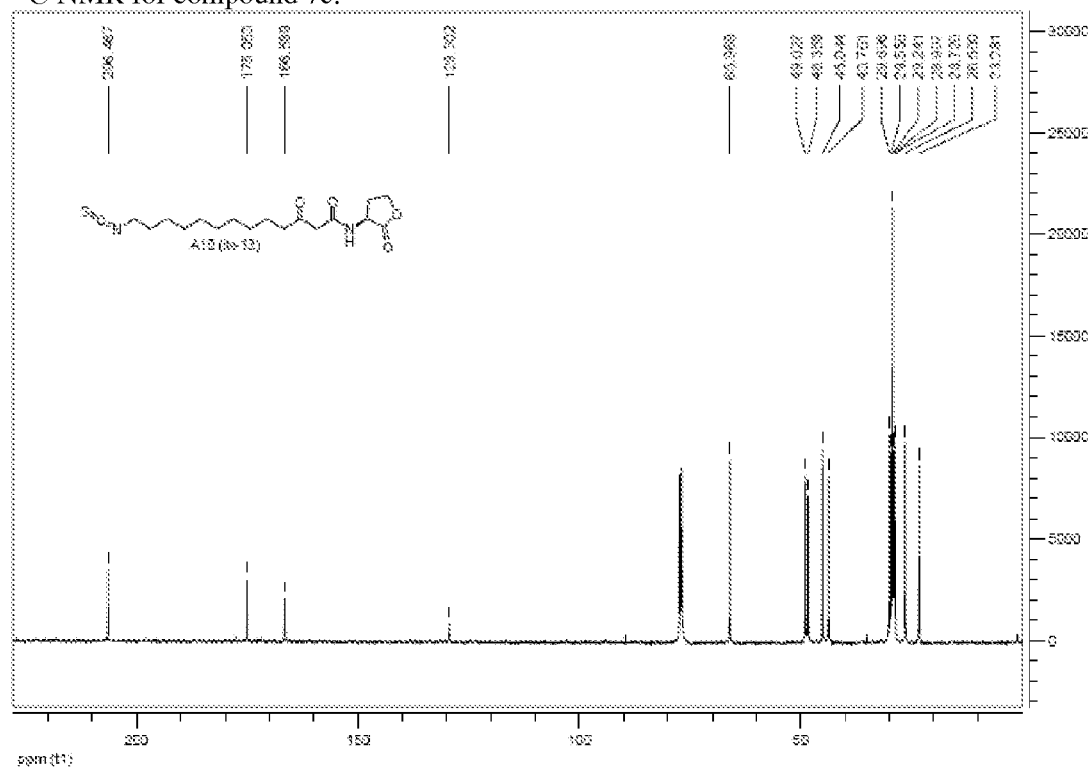

Figure 3G1
$^{13}$C DEPT-NMR for compound 7c:
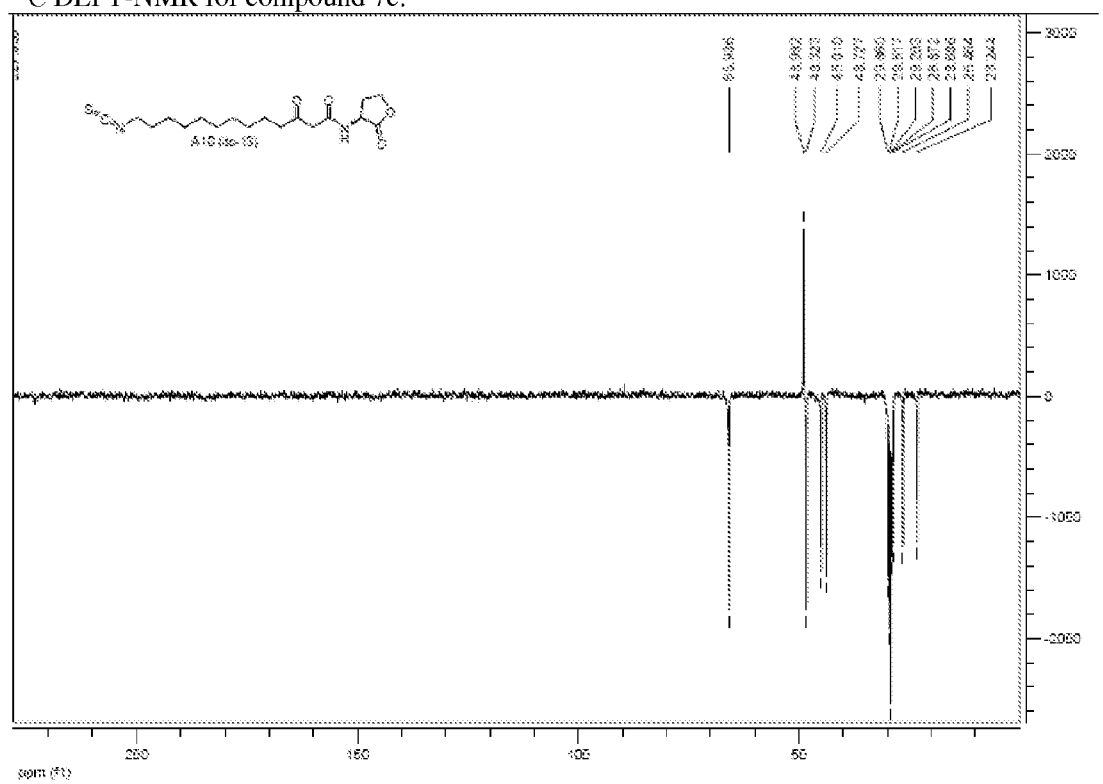

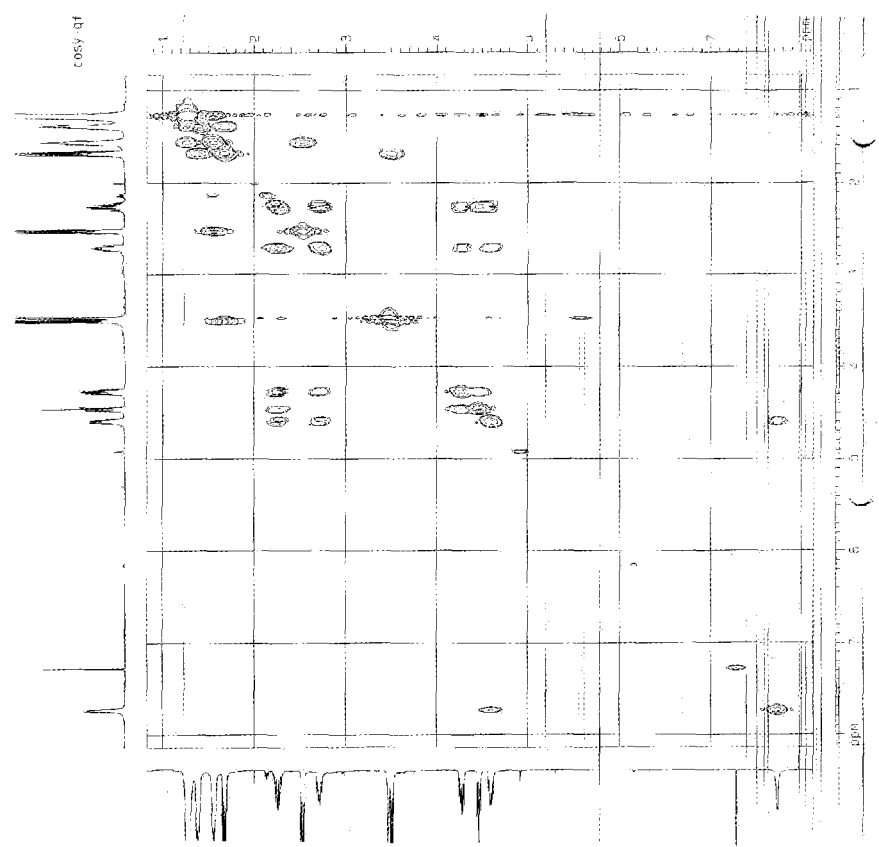
Figure 3G2
2D COSY-NMR for compound 7c:

a b

COVALENT INHIBITION OF BACTERIAL QUORUM SENSING

This application is a continuation of U.S. application Ser. No. 13/381,952, filed Feb. 16, 2012, now U.S. Pat. No. 8,501,969, issued Aug. 6, 2013, which is a U.S. national phase of International Application No. PCT/IB2010/053061 filed Jul. 4, 2010 which designated the U.S. and claims priority to U.S. Provisional Application No. 61/222,944, filed Jul. 3, 2009, the entire contents of each of which are incorporated herein by reference.

FIELD OF THE INVENTION

The present invention relates to inhibitors of bacterial communication, and methods of use and manufacture thereof.

BACKGROUND OF THE INVENTION

Chemical coordination of gene expression among bacteria as a function of population density is regulated by a mechanism known as 'quorum sensing' (QS). Cell-to-cell communication enables single cell organisms to coordinate their behavior so as to adapt to changing environments, allowing them to compete, as well as coexist, with multicellular organisms. Examples of QS-controlled behaviors include biofilm formation, virulence factor expression, antibiotic production and induction of bioluminescence. These processes are beneficial to a bacterial population only when carried out simultaneously. For example, bioluminescence produced by the marine bacterium *Vibrio fischeri* is beneficial to a number of organisms that host this species but only if a sufficient number of bacteria synchronize their light emission. While various QS signaling systems have been discovered, more proteins and small molecules involved in QS remain to be described (1-4).

The importance of QS in bacteria and its effect on human health is significant, especially when one considers that the total microbial population in the human adult is estimated to exceed the number of mammalian cells by at least a factor of ten. The gastrointestinal tract alone contains 500-1000 different species presenting great genetic diversity, and since most of these species have not yet been cultured in vitro, this population has barely been characterized. Intra- and interspecies QS may very well aid this commensal population in coordinating important processes, such as maintenance of population size and aiding or preventing pathogenic bacterial colonization (5, 6).

QS is regulated by autoinducers that can be categorized into several classes, depending on shared molecular features (FIG. 1a, 2-4). More than 70 species of Gram-negative bacteria employ N-acyl homoserine lactones (AHLs) as autoinducers, with differences within this class of QS signals occurring in the length and oxidation state of the acyl side chain. Various AHLs from different species have been shown to play important roles in bacterial infections. An important example is the Gram-negative bacterium, Pseudomonas aeruginosa. This common environmental microorganism is an opportunistic human pathogen, being prominent, for example, in patients suffering from cystic fibrosis (CF), a common and lethal inherited genetic disorder, where patients often die due to impaired lung defense functions. A key factor contributing to the pathogenesis and antibiotic resistance of *P. aeruginosa* lies in its ability to form a biofilm, a microbially-derived sessile community of cells that attach either to an interface or to each other, inhabit an extracellular polymeric matrix, and exhibit a phenotype distinct from that of planktonic cells with respect to growth, gene expression, and protein production. Although the formation and specific architecture of biofilms are regulated by various QS systems (7), as well as other factors, such as cyclic di-GMP, it has been shown that inhibition of even a single QS regulator can lead to a significant decrease in overall biofilm formation.

The primary QS system in *P. aeruginosa* is regulated through the synthesis and secretion of 3-oxo-C12-HSL, which, upon reaching a threshold concentration, binds the transcriptional activator LasR. This interaction has been proposed to lead to correct folding, followed by dimerization and binding of the LasR dimer to its target DNA, resulting in gene expression. In addition, several other small molecules have been found to play a role in the regulation of gene expression (e.g. C4-HSL, PQS), although the signaling events initiated by 3-oxo-C12-HSL recognition appear to be at the top of the QS hierarchy (8-10). Due to its medical importance, QS in *P. aeruginosa* has been extensively studied. One notable breakthrough in this field came with the determination of the crystal structure of LasR bound to its natural ligand (3-oxo-C12-HSL), recently reported by Bottomley et al.(11).

Interfering with QS signaling has been explored in recent years as a novel approach to combat pathogenesis. Several groups have identified compounds showing significant inhibition of QS in *P. aeruginosa*, although the number of strong inhibitors resulting from such efforts remains low. Examples of moderately potent inhibitors, with their $IC_{50}$ values, are shown in FIG. 1b.

SUMMARY

The background art does not teach or suggest sufficiently effective inhibitors of bacterial communication, and methods of use and manufacture thereof.

The present invention, in at least some embodiments, overcomes these drawbacks of the background by art by providing covalent inhibitors of bacterial communication, and methods of use and manufacture thereof. The inhibitors may optionally act directly or indirectly to inhibit bacterial communication, and may also optionally act at any stage of bacterial communication.

According to at least some embodiments, these inhibitors are inhibitory compounds (small molecules), which comprise a reactive group, preferably an electrophile capable of forming a covalent bond with a nucleophile in the active site of its target protein, that does not interact non-specifically with other proteins. The reactive group is preferably connected to a moiety that is able to interact with the target protein in a manner which permits the reactive group to interact with the nucleophile and hence to form the covalent bond. Such inhibitors preferably have the formula A-B, in which A is an electrophilic functional group and B is the natural ligand of the target protein or a portion thereof, such that the inhibitor is able to interact with the target protein in such a manner that the A functional group is able to covalently bind to the target protein and hence to inhibit binding of the natural ligand.

According to some embodiments there is provided a set of electrophilic probes (inhibitors) designed to covalently bind to a protein for which the natural ligand is a homoserine lactone which acts in quorum sensing. Homoserine lactones are known to act as ligands for quorum sensing for Gram-negative bacteria. Non-limiting examples of bacteria for which quorum sensing may optionally be inhibited by one or more compounds of the present invention include one or more of *Acinetobacter, Actinobacillus, Agrobacter, Bordetella, Brucella, Campylobacter, Cyanobacteria, Enterobacter, Erwinia, Escherichia coli, Franciscella, Helicobacter,*

*Hemophilus, Klebsiella, Legionella, Moraxella, Neisseria, Pasteurella, Proteus, Pseudomonas, Salmonella, Serratia, Shigella, Treponema, Vibrio* and *Yersinia*.

As a non-limiting example, the protein may optionally feature a LasR binding pocket as for *P. aeruginosa*, but optionally the protein may be any type of protein for which the natural ligand is a homoserine lactone, as long as inhibition of the protein's activity leads to specific inhibition of QS-regulated gene expression and concomitant reduction of virulence factor secretion and biofilm formation. Thus, B is optionally any homoserine lactone moiety.

Without wishing to be limited by a single hypothesis or by a single example, it is believed that these compounds covalently bind to Cys79 of the LasR binding pocket. For this non-limiting example, B is a 3-oxo-$C_{(n+2)}$—N-acyl homoserine lactone moiety, in which n is at least 2 and is optionally up to 14, and A is any suitable electrophilic functional group. Unless otherwise explicitly stated, all of the molecules are assumed to be the S enantiomer.

According to at least some embodiments there is provided a compound of formula I:

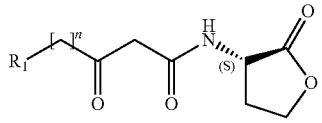

in which n represents the number of carbons (optionally n=1-18 although in various embodiments this range may be altered; as described in greater detail below the term "n=a-b" means that n is any number that is selected from the group consisting of a, a+1 . . . b; the term "m" as used herein is given similar meaning for the range of numbers provided), and $R_1$ is any suitable reactive electrophilic functional group. Optionally $R_1$ is selected from the group consisting of a thiol, an isocyanate, an isothiocyanate, an isoselenocyanate, a substituted or unsubstituted reactive amide functional group, NHC(=O)C=N—$NH_2$, a reactive substituted cyclic moiety, a reactive substituted or unsubstituted heterocycle (which optionally has at least one unsaturated bond), an alkyl sulfonate (in which the alkyl sulfonate in combination with the B moiety forms an alkyl sulfonic ester), a substituted alkene, a reactive amine and $R_3$. As used herein, cyclic encompasses both aromatic and non-aromatic.

If the thiol is present, n=5-12. A non-limiting example of a structure featuring a thiol according to at least some embodiments of the present invention is shown in Structure-D.

The isocyanate is optionally substituted or unsubstituted. Preferably, the isocyanate is unsubstituted. As a specific non-limiting example, n=9 (as shown in structure-Q below).

The isothiocyanate is optionally substituted or unsubstituted, in which substituted isothiocyanate optionally has the structure $R_2N=C=S$, in which $R_2$ is selected from the group consisting of substituted alkyl, substituted isoalkyl, substituted alkene and substituted isoalkene, each of which is optionally and preferably substituted with a moiety selected from the group consisting of halogen, a heterocyclic amine, and an alkylamine. If the substitution is a heterocyclic amine, it is preferably selected from the group consisting of a pyridyl, a pyrrolyl, pyrrolidine, an arylamine, an imidazolyl and a piperidine.

According to at least some embodiments, $R_2$ is selected from the group consisting of substituted ethylene, substituted propylene, substituted butene and substituted pentene, optionally including any isomer thereof, which may optionally be substituted as described above; more preferably, $R_2$ is substituted 2-pentene, which is more preferably substituted with one of alkylamine, pyridyl, pyrrolyl, arylamine or imidazolyl; most preferably n=1-5 (as shown in structure-Y below).

According to at least some embodiments, $R_2$ is selected from the group consisting of substituted ethyl or methyl, optionally substituted as described above but preferably substituted with one of alkylamine, pyridyl, pyrrolyl, arylamine, piperidine or imidazolyl; and more preferably substituted with piperidine. Most preferably, the substitution is with piperidine and n=1-5 (as shown in structure-Z1, structure-Z2 and structure Z-3 below).

If substituted with halogen according to at least some embodiments, preferably the halogen is bromine or chlorine. Most preferably $R_2$ is bromoalkyl or chloroalkyl and n=7-9; most preferably n=8 (corresponding to structure-3). If the isothiocyanate is unsubstituted, then preferably n=8-10 (corresponding to structures itc-11, itc-12 and itc-13).

The reactive amide functional group is optionally a halocarboxamide which is preferably selected from the group consisting of a bromocarboxamide and a chlorocarboxamide, in which the carbon chain of the amide functional group is from 1 to 16 carbons in length; preferably n=5-16. More preferably the halocarboxamide is a haloacetamide which is most preferably selected from the group consisting of a bromoacetamide and a chloroacetamide, in which preferably n=5-16 (corresponding to structures hal-11-Br, hal-12-Br, hal-13-Br, hal-11-Cl, hal-12-Cl and hal-13-Cl).

If $R_1$ is NHC(=O)C=N—$NH_2$, preferably n=5-16 (as shown for example in structure-4).

The reactive substituted cyclic moiety is preferably selected from the group consisting of substituted alkylenecyclobutane, alkylenecyclopentane and alkylenecyclohexane, which are more preferably selected from the group consisting of alkylenecyclobutane dione, alkylenecyclopentane dione and alkylenecyclohexane dione, and which are most preferably alkylenecyclobutane-2,4-dione, alkylenecyclopentane-2,4-dione and alkylenecyclohexane-2,4-dione; the alkylene moiety is optionally methylene, ethylene, butene or pentene and is preferably methylene. Most preferably the reactive substituted cyclic moiety is methylenecyclopentane-2,4-dione and optionally n=5-16, but more preferably n=8-10 (as shown in structure-8).

If unsubstituted, the reactive heterocycle is preferably ethylene oxide and n=5-16; more preferably n=8-12; most preferably n=9-11 (as shown in structure-12).

If substituted, the reactive heterocycle preferably has at least one unsaturated carbon bond, and is selected from the group consisting of 2-furanone, and a pyranone (which may optionally be 2-pyrone or 4-pyrone). If the reactive heterocycle is 2-furanone, optionally n=5-16, preferably n=8-12; more preferably n=9-11 (as shown in structure-13). If the reactive heterocycle is 2-pyrone, optionally n=5-16, preferably n=8-12; more preferably n=9-11 (as shown in structure-14).

The alkyl sulfonate is selected from the group consisting of substituted and unsubstituted alkyl sulfonates; preferably the alkyl sulfonate is selected from the group consisting of methyl sulfonate, ethyl sulfonate, propyl sulfonate and butyl sulfonate; more preferably the alkyl sulfonate is propyl sulfonate and n=1-14, more preferably n=5-9; most preferably the alkyl sulfonate is propyl sulfonate and n=6-8 (as shown in structure-9). If substituted, the alkyl sulfonate is preferably a haloalkyl sulfonate, more preferably selected from the group consisting of bromoalkyl sulfonate, fluoroalkyl sulfonate and chloroalkyl sulfonate; and is most preferably selected from the group consisting of bromomethyl sulfonate, chloromethyl sulfonate and fluoromethyl sulfonate, in which preferably n=1-14, more preferably n=5-9; most preferably n=6-8 (as shown in structure-X, which also shows the unsubstituted alkyl sulfonate); or alternatively, is most preferably selected from the group consisting of 3-bromopropyl sulfonate, 2-bromopropyl sulfonate, 3-chloropropyl sulfonate and 2-chloropropyl sulfonate, in which preferably n=1-14, more preferably n=5-9; most preferably n=6-8 (as shown in structure-7).

The substituted alkene is preferably selected from the group consisting of substituted ethylene, preferably substituted with a halogen which is more preferably bromine; and C=C=CH$_2$R$_5$, in which R$_5$ is a halogen, preferably bromine. If the substituted alkene is C=C=CH$_2$R$_5$, then R$_5$ is preferably bromine and preferably n=1-14, more preferably n=5-9; most preferably n=8-10 (as shown in structure-10 below).

In some embodiments, the reactive amine is an alkyl amine or a dialkyl amine, in which the alkyl moiety or moieties are preferably substituted, more preferably with a halogen. The alkyl moiety is preferably selected from the group consisting of methyl, ethyl, propyl and butyl; more preferably, the reactive amine is a halogen substituted diethylamine. Most preferably, the reactive amine is a chlorine substituted diethylamine and preferably n=1-14, more preferably n=5-9; most preferably n=8-11 (as shown in structure-16).

R$_3$ is optionally selected from the group consisting of:

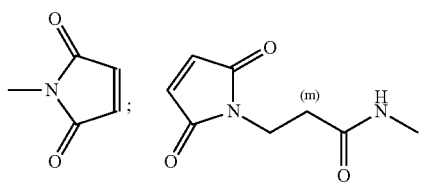

in which m=1-6; preferably m=1;

And

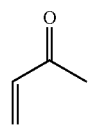

If R$_3$ is

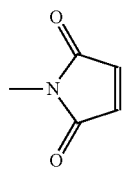

then optionally n=1-14, more preferably n=7-11, and most preferably n=8-10 (as shown in structure-5).

If R$_3$ is

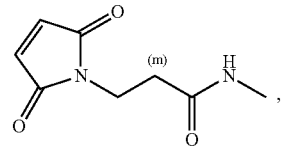

then preferably n=3-7 and more preferably n=4-6; most preferably n=4-6 and m=1 (as shown in structure-6).

If R$_3$ is

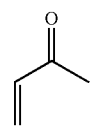

then preferably n=9-11 (as shown in structure-15).

According to other embodiments of the present invention, there is provided a compound of formula II:

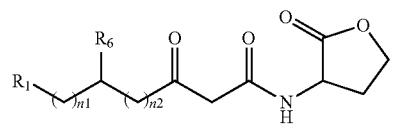

In which R$_1$ is optionally any group as recited above, R$_6$ can be alkylamine, pyridyl, pyrrolyl, arylamine, imidazolyl or piperidine; m=0-8; and n$_2$=0-8 (n$_1$ and n$_2$ are each independently selected). Exemplary structures are shown as Structure-P1, Structure-P2, Structure-P3, Structure-P4 and Structure-P5.

Any of the above compounds may optionally comprise a disulfide bond in the carbon chain of the backbone, as shown for example with regard to Structure-C.

Any one or more of the above compounds may optionally be used in various applications according to various embodiments of the present invention for which inhibition of quorum sensing is desired, including but not limited to treatment of plant or animal diseases (in which animal may optionally comprise any mammal, fish, reptile or bird; preferably the animal is a mammal and optionally the animal is a human); medical devices, including implantable medical devices as well as those outside of the body, or interfacing with the body and the external environment; any type of structure which carries and/or is placed an aqueous fluid; membranes, textiles, packaging materials, or for prevention or reduction of formation of any type of biofilm.

As used herein, the term "biofilm" refers to a thin layer of microorganisms adhering to the surface of a structure, which may be organic or inorganic, together with the polymers that they secrete.

Non-limiting examples of medical devices include coatings on natural tissues (including teeth), catheters, pacemakers, contact lenses, stents, heart valve replacements or augmenting devices, implantable automatic defibrillators, artificial heart assist devices, implantable infusion pumps, drainage devices, artificial joints, bone pins, screws and other orthopedic devices, crowns, dental fillings, dental implants, other dental or orthodontic devices, endodontic instruments, surgical sutures, clips and staples or other fasteners, surgical meshes, intraocular lenses, buttresses, lapbands, bandages, grafts, stent/grafts, knotless wound closures, sealants, adhesives, tissue scaffolds, soft tissue replacement or augmentation implants (including but not limited to breast, cheek and buttock implants) and the like.

As used herein, the term "catheter" includes but is not limited to catheters, catheter lines, ports, shunts, feeding tubes, endotracheal tubes and peripheral inserted central catheter (PICC) lines.

Non-limiting examples of structures carrying aqueous fluids include tubing, water filters and other purification devices, containers for such fluids, manufacturing facilities which feature surfaces that contact aqueous fluids (including without limitation pipes, tubes, containers, machinery), clean room surfaces, any type of pipes, tubes, containers and machinery in a building in which humans may be present, and the like.

Non-limiting examples of structures placed in an aqueous fluid include filters, machinery, underwater structures, marine vessels, and any structure located in a marine environment (and particularly but not exclusively submerged in a marine environment).

According to at least some embodiments, there is provided a composition comprising a compound according to any of the above claims in a suitable carrier. Optionally the composition further comprises one or more of dyes, antimicrobial agents, growth factors, or anti-inflammatory agents. Also optionally the composition may further comprise an additional excipient.

BRIEF DESCRIPTION OF THE DRAWINGS

The present invention will be understood and appreciated more fully from the following detailed description, taken in conjunction with the drawings in which:

FIGS. 3A-3C show a non-limiting exemplary synthesis scheme of some inhibitory compounds. DMF, dimethyl formamide; DCC, N,N'-dicyclohexyl-carbodiimide; DMAP, 4-dimethylamino pyridine; DCM, dichloromethane; TFA, trifluoroacetic acid, while FIGS. 3D1, 3D2, 3E1, 3E2, 3F1, 3F2, 3G1 and 3G2 show NMR graphs for the resultant products.

DESCRIPTION OF SOME EXEMPLARY EMBODIMENTS

The present invention, in at least some embodiments, provides covalent inhibitors of bacterial communication, and methods of use and manufacture thereof. Without wishing to detract from the scope or generality of the present invention as described and claimed, the below description focuses on those embodiments related to the compounds of Formulas I and II, their uses and methods of synthesis thereof.

As described above, these inhibitors inhibit bacterial communication, including quorum sensing, for bacteria including but not limited to *P. aeruginosa*. Without wishing to be limited by a single hypothesis, it is possible that at least some of these inhibitory compounds have a sufficiently similar structure to a natural homoserine lactone compound that activates LasR or an equivalent protein, such as for example 3-oxo-$C_{12}$-HSL for *P. aeruginosa*, thereby obviating past observations that small changes to the structure of 3-oxo-$C_{12}$-HSL can lead to a large reduction in affinity. These inhibitor compounds are believed to present only a minimal deviation from the parent autoinducer and contain a small reactive moiety that can covalently bind a residue in the LasR binding pocket or equivalent protein. Such covalent probes would be expected to compete effectively with the natural compound for binding to LasR or an equivalent protein, such that their slightly altered occupation of the binding pocket upon conjugation would likely result in a conformational change that is less than optimal for effective binding of the transcriptional activator to its target DNA. Use of this type of probe could also severely affect the regulation and recycling of both LasR or an equivalent protein and the natural ligand such as 3-oxo-$C_{12}$-HSL.

Figure 1:
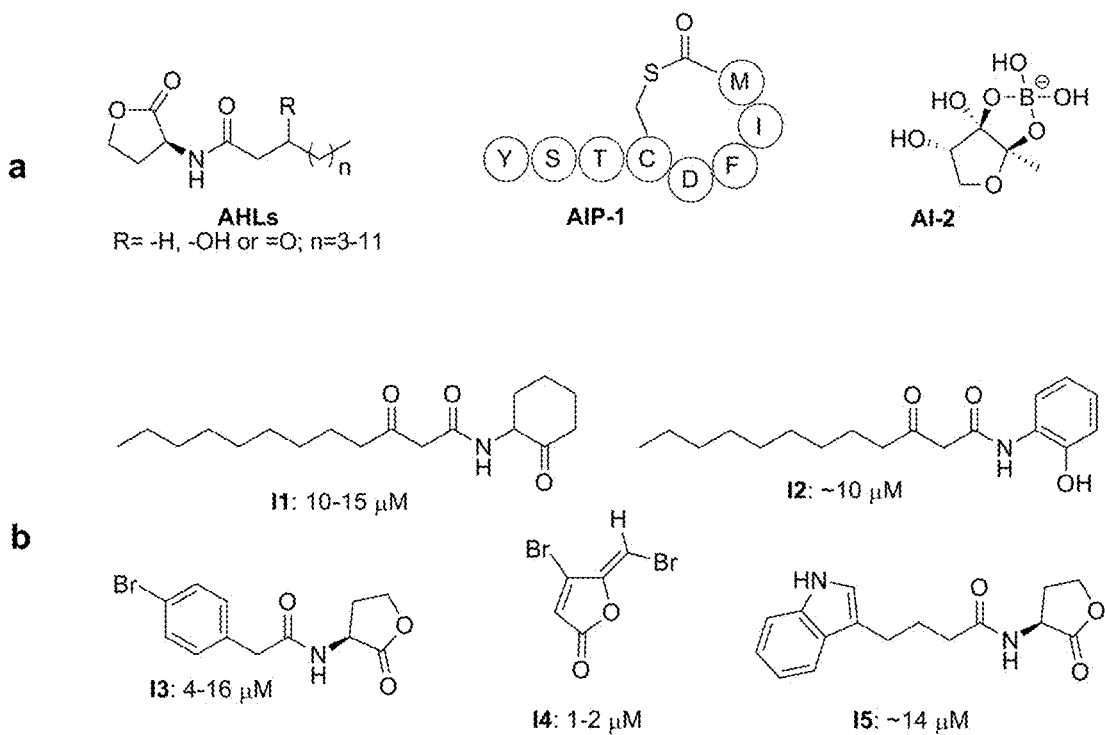
FIG. 1 shows a) Examples of bacterial autoinducers belonging to distinct structural classes; b) Examples of synthetic QS inhibitors in *P. aeruginosa* (I1-I5). Approximate IC50 values (from different reporter assays) are listed below the compounds.
Figure 2:
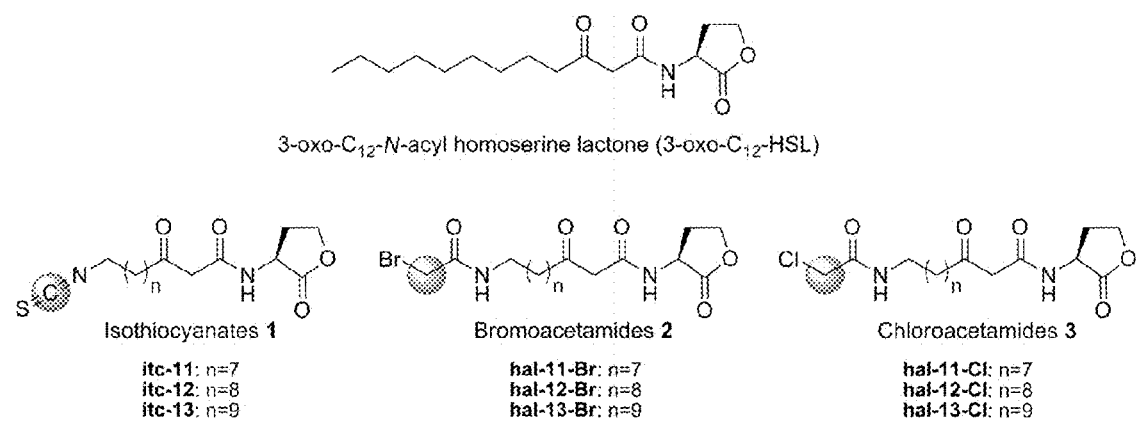
FIG. 2 shows structures of the natural autoinducer of *P. aeruginosa*, 3-oxo-C12-N-acyl homoserine lactone (3-oxo-C12-HSL), and non-limiting examples of nine synthetic analogues classified as isothiocyanates (1) bromoacetamides (2) or chloroacetamides (3). Electrophilic carbons are marked (grey circles) for each reactive group.

Some non-limiting examples of these electrophiles with different functional groups and different alkyl chain lengths (isothiocyanates 1, bromoacetamides 2, chloroacetamides 3) are shown in FIG. 2, in comparison to the natural ligand. One of the many challenges is to design a probe that would be sufficiently reactive so as to react with the nucleophilic cysteine but not so overly reactive that unwanted reactions would take place with other residues before the probe reaches the binding pocket.

Further specific non-limiting examples of compounds of Formulas I and I are shown below.

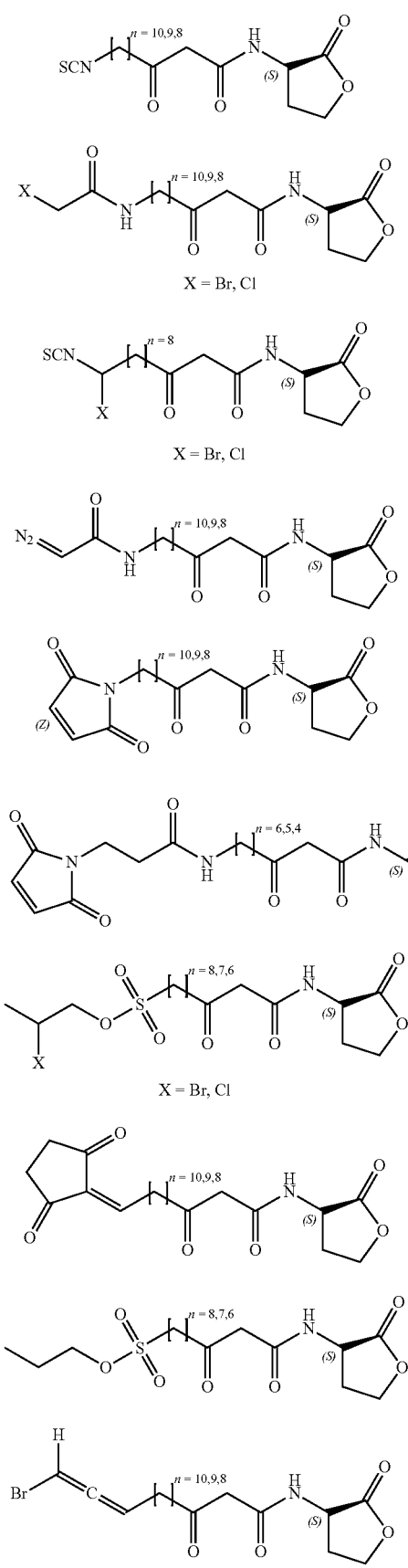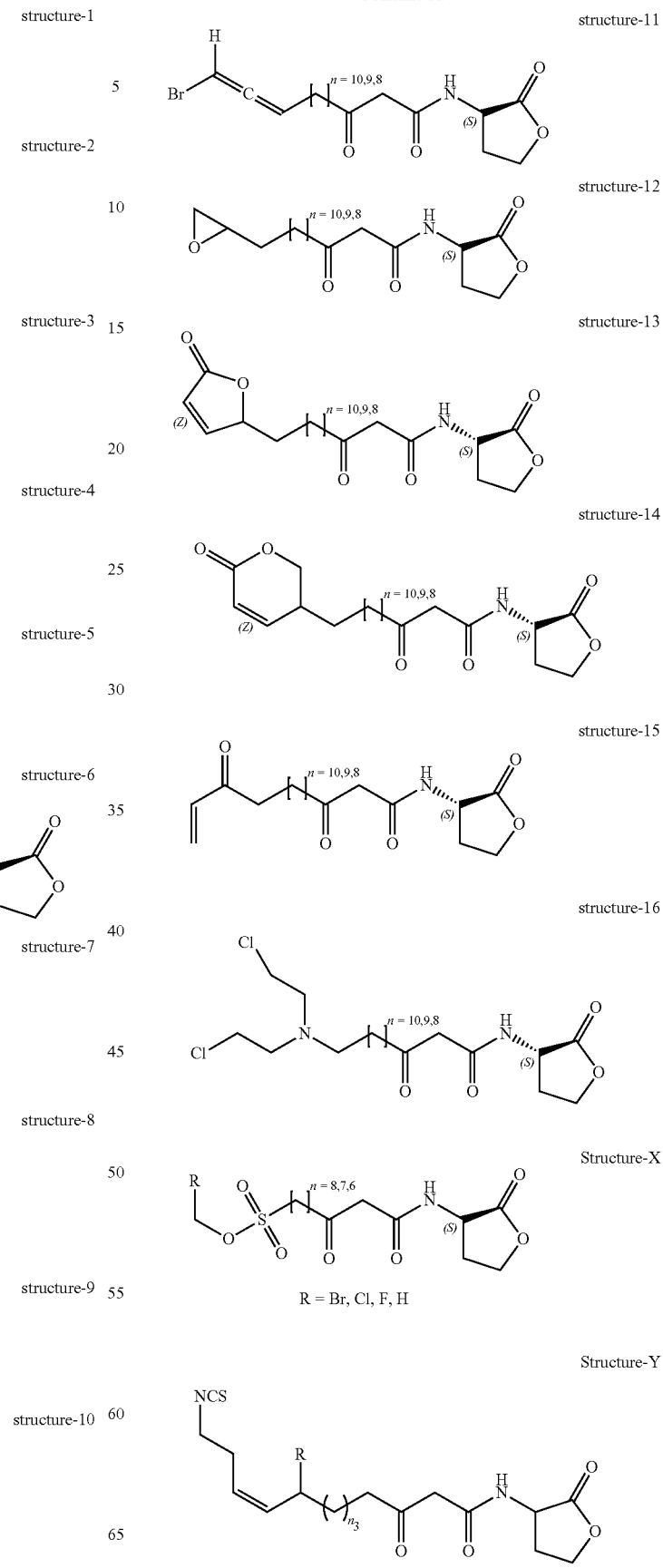

Structure-Z1

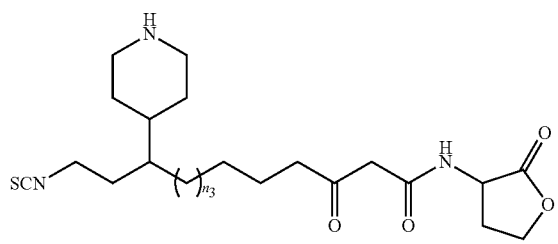

Structure-P-1

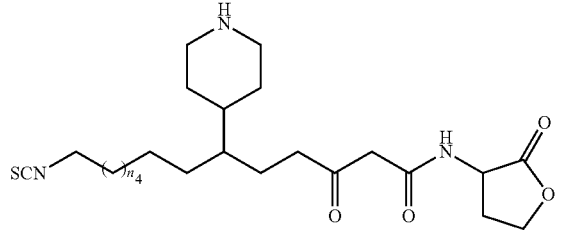

Structure-Z2

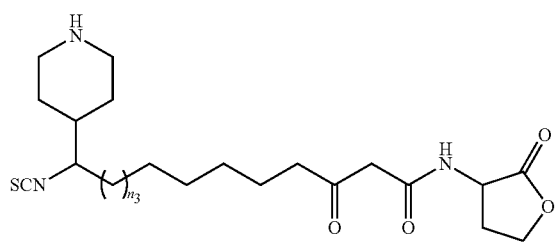

Structure-P2

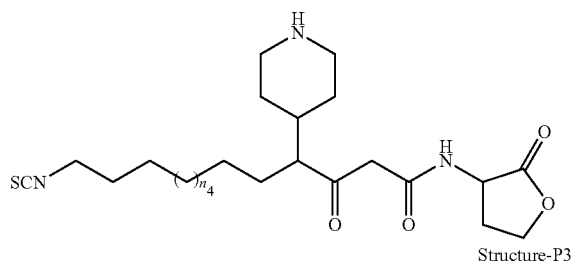

Structure-Z3

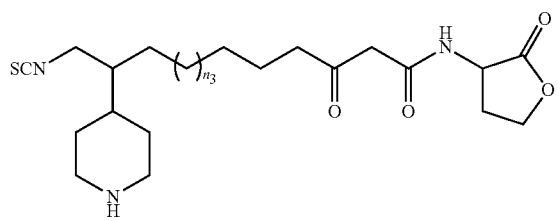

Structure-P3

Structure-P4

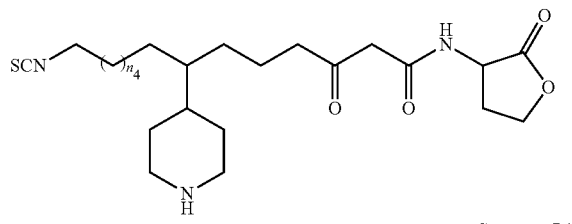

For Structure-Y and Structures-Z1-Z3 shown above, $n_3$ is selected such that $n_3=n-1$ for Structure-Y, $n_3=n-3$ for Structure-Z1 and Structure-Z3, and $n_3=n-5$ for Structure-Z2; wherein n is set as described above.

Structure-P5

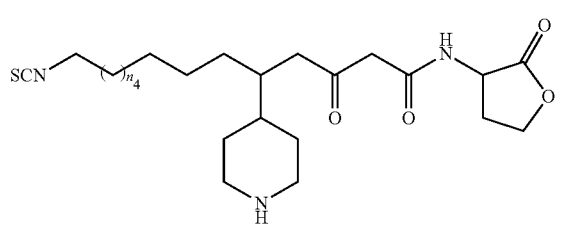

Structure-Q

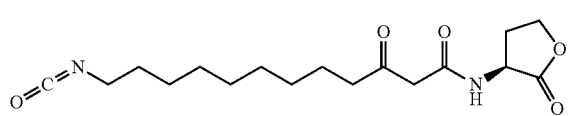

For Structures-P1-P5 shown above, $n_4$ is selected such that $n_4=n-5$ for Structure-P1 and Structures P3-P5, and $n_4=n-3$ for Structure-P2; wherein n is set as described above.

Structure-C

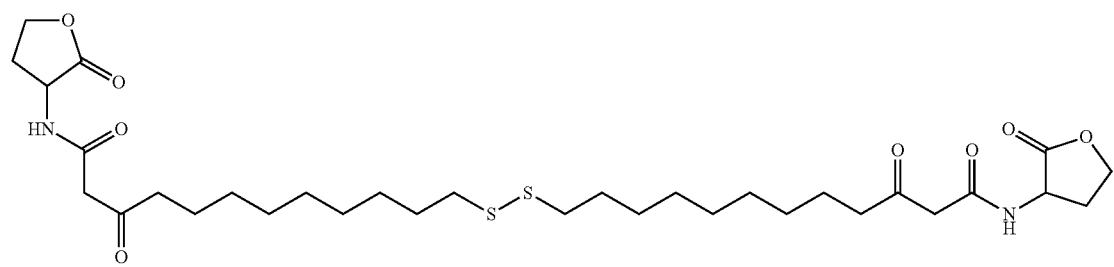

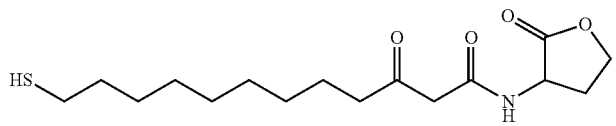

Sztructure-D

EXAMPLES

The principles and operation of the compositions and methods according to the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Various embodiments, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Example 1

Synthesis of Isothiocynates and Haloacetamides Compounds of Formula I

Figure 3A:
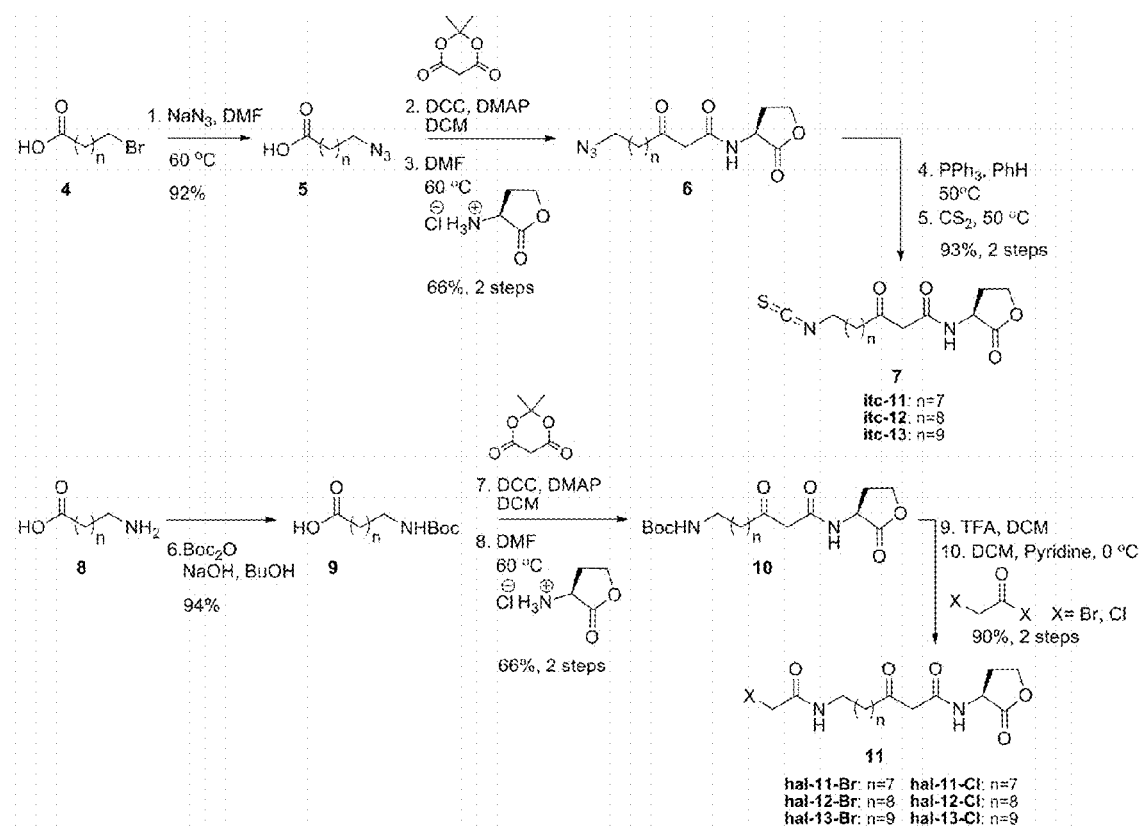
Figure 3B:
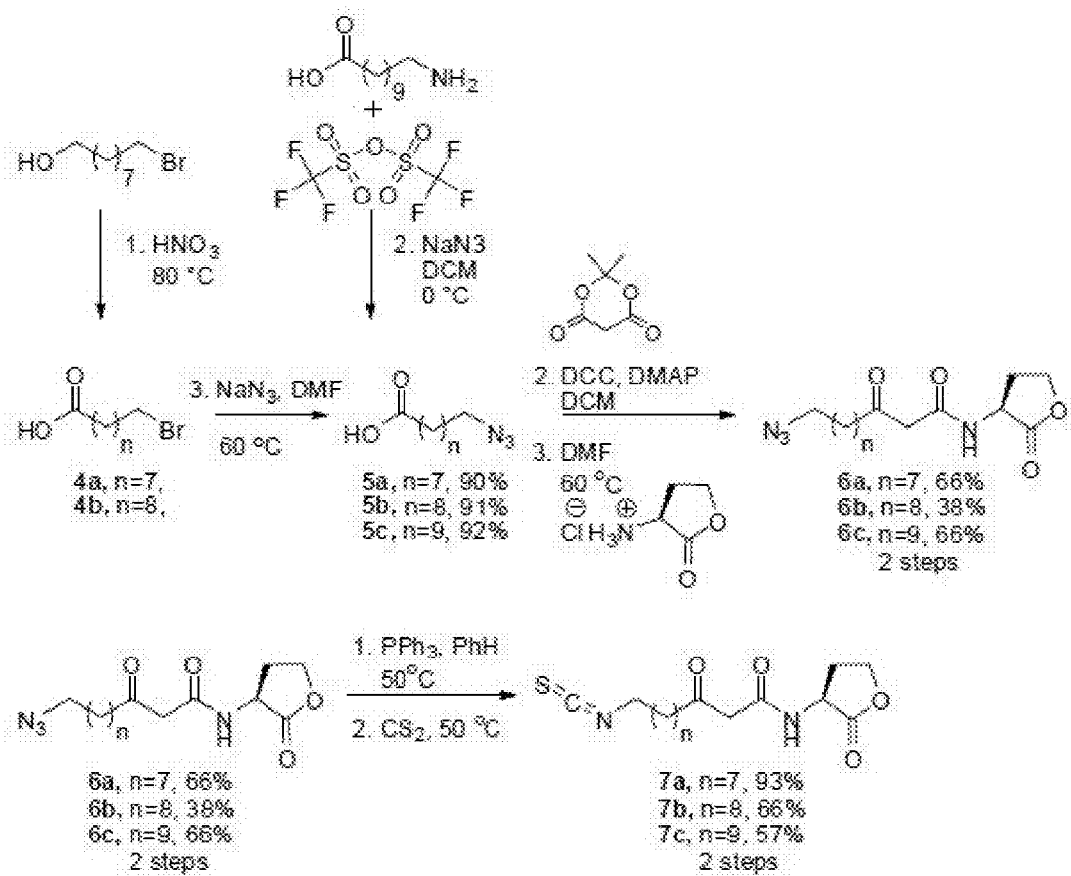
Figure 3C:
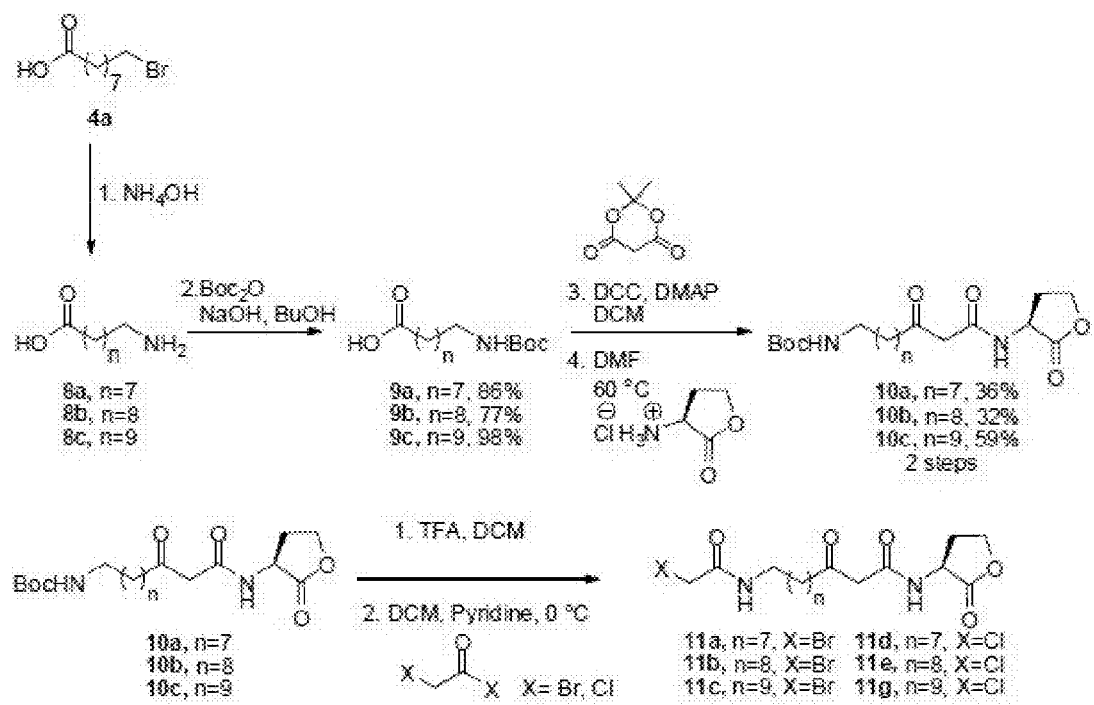

This non-limiting Example relates to syntheses of isothiocyanates itc-11,12,13 and haloacetamides hal-11,12,13-Br and hal-11,12,13-Cl. The schematic outline of the synthesis is shown in FIG. 3A; FIG. 3b shows a more specific synthesis for the isothiocynate compounds of Formula I (DCM is dichloromethane, DMF is dimethylformamide, DCC is N,N' dicycohexyl carbodiimide, DMAP is 4-dimethylamino pyridine); FIG. 3c shows a more specific synthesis for the haloacetamide compounds of Formula I (DCM is dichloromethane, DMF is dimethylformamide, DCC is N,N' dicycohexyl carbodiimide, DMAP is 4-dimethylamino pyridine, TCA is trifluoroacetic acid).

General

All chemical reagents were purchased from Aldrich or Acros and used without further purification. Trypsin was purchased from Promega industries (V5280). Thin-layer chromatography as performed on TLC aluminum sheets silica gel 60 with F254 indicator (Merck). Flash chromatography was performed on Merck 40-63 μm silica gel. Solvent ratios for the purification of compounds by flash chromatography are reported as percent volume (v/v). SDS page was done using a NuPAGE Surelock Xcell, on NuPAGE Novex Bis-Tris Pre-Cast gels purchased from Invitrogen (NP0342). Expression was done either at small scale, using Ni-NTA spin columns 1314, QIAGEN) or at large scale using Ni2+ prepacked cartridge (Bio-Scale, Mini Profinity AC cartridge, 732-4612, BIO-RAD) fitted to an AKTAprime plus purification system (GE Healthcare). NMR analyses were performed using a Bruker Avance DPX200 or, alternatively using a Bruker Avance DMX500. Spectra were calibrated on residual solvent signal. Analytical HPLC analyses were performed on a Surveyor Plus HPLC System (Thermo Scientific) using a Luna C18, μm (150×4.6 mm) column at a flow rate of 1 mL/min. Preparative HPLC was routinely performed on Sapphire 600 instrument (ECOM) using a Luna C18 column, 10 μm (250×21.20 m), at a flow rate of 20 mL/min. All runs used linear gradients of 0.1% aqueous TFA (solvent A) 90% acetonitrile containing 0.1% TFA (solvent B). Compounds were identified by UV detection dual wavelengths (230 nm, 260 nm). All MS analyses were performed on a LCQ Fleet mass spectrometer (Thermo Scientific) with an ESI source. Spectra were collected in the positive ion mode and analyzed by Xcalibur software (Thermo Scientific). Microtiter plate based bioassays were evaluated using a SpectraMax M2 spectrophotometer (Molecular Devices). Compounds 3-oxo-C12-SL and 4-Br-PHL were synthesized following modifications of procedures described by Chhabra al.1 and Geske et al.2 (4-bromophenylacetic acid was reacted with homoserine lactone hydrobromide through EDC/NHS mediated coupling), respectively.

Detailed Synthetic Procedures

9-Bromanoic Acid (4a)—

To a solution of concentrated nitric acid (10 mL, 258 mmol) 9-bromononanol (1 gr, 4.48 mmol) was added over a period of 30 minutes, maintaining a temperature of 25-30° C. The solution was stirred at room temperature for 4 hours, then heated to 80° C. and stirred for an additional hour. The reaction mixture was then cooled back to room temperature and diluted carefully with 100 mL of distilled water. The product was extracted with diethyl ether (4×25 mL) after which the organic phases where combined and dried over magnesium sulfate. The mixture was then filtered and concentrated in vacuo to yield product 4a quantitatively. $^1$H-NMR (200 MHz, CDCl$_3$): 1.3-1.5 (m; 8H), 1.59-1.71 (m; 2H), 1.78-1.92 (m; 2H), 2.36 (t; J=7.4 Hz; 2H), 3.40 (t; J=6.8 Hz; 2H), 9.8 (m, 1H).

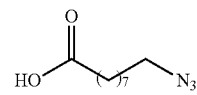

9-Azidononanoic Acid (5a)—

9-bromononanoic acid (4a) (1.062 gr, 4.48 mmol) was dissolved in 15 mL of dry dichloromethane. Sodium azide (914 mg, 14 mmol) was then added and the mixture was stirred at 60° C. for 6 hours. The solution was cooled and diluted with 50 mL of dichloromethane and then washed with 1 M HCl (5×50 mL), brine (2×50 mL) and dried over magnesium sulfate. The mixture was then filtered and concentrated in vacuo to yield 90% of product 5a as a white solid.

$^1$H-NMR (200 MHz, CDCl$_3$): 1.3-1.5 (m; 8H), 1.5-1.7 (m; 4H), 2.33 (t; J=7.4 Hz; 2H), 3.25 (t; J=6.86 Hz; 2H).

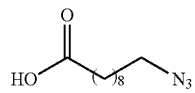

10-Azidodecanoic Acid (5b)—

10-bromodecanoic acid (1.125 gr, 4.48 mmol) was reacted as described for product 5a to yield 91% of product 5b. $^1$H-NMR (200 MHz, CDCl$_3$): 1.2-1.5 (m; 10H), 1.5-1.7 (m; 4H), 2.35 (t; J=7.41 Hz; 2H), 3.24 (t; J=6.81 Hz; 2H).

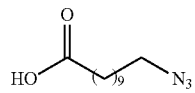

11-Azidoundecanoic Acid (5c)—

Sodium azide (2.38 gr, 44.3 mmol) was dissolved in 7.5 mL of water and added to a round bottom flask containing 15 mL of dichloromethane. The flask was cooled to 0° C. and trifluoromethanesulfonic anhydride (1.5 mL, 8.9 mmol) was added dropwise. The resulting solution was allowed to warm to room temperature and was stirred for two hours. The aqueous layer was extracted with dichloromethane (3×8 mL), and the combined organic phases were washed with a saturated solution of sodium carbonate. The resulting solution was then slowly added to a suspension of 11-aminoundecanoic acid (892 mg, 4.43 mmol), K$_2$CO$_3$ (915 mg, 6.62 mmol), and CuSO$_4$.5H$_2$O (11 mg, 0.0044 mmol) in 15 mL of water and 22.5 mL of methanol. The mixture was stirred overnight, and concentrated in vacuo. The solution was acidified with 1 M HCl solution and extracted with dichloromethane (4×50 mL). The organic phases where combined, dried with magnesium sulfate, filtered and concentrated in vacuo, yielding 5c at 92%. $^1$H-NMR (200 MHz, CDCl$_3$): 1.25-1.4 (m; 12H), 1.5-1.7 (m; 4H), 2.35 (t; J=7.43 Hz; 2H), 3.25 (t; J=6.88 Hz; 2H).

General Procedure for Boc-Protection of an Amine

To a round bottom flask containing water (9 mL), NaOH (800 mg, 19.5 mmol), tert butanol (9 mL) and Boc anhydride (4.3 gr, 19.5 mmol), the desired amine (18.55 mmol) was added. The mixture was then stirred at room temperature for 16 hours, after which it was diluted with water (20 mL) and 1 M HCl (10 mL). The resulting solution was extracted with ethyl acetate (1×60 mL+2×20 mL), washed with brine and dried over magnesium sulfate. The crude mixture was filtered and concentrated in vacuo.

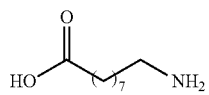

9-Aminononanoic Acid (8a)—

9-bromodecanoic acid (2.0052 gr, 8.46 mmol) was added to a round bottom flask containing 80 mL of aqueous ammonium hydroxide (25% NH$_3$). The resulting mixture was stirred for 24 hours at room temperature, after which the aqueous solution was evaporated under reduced pressure, resulting in product 8a as a white solid at quantitative yield. $^1$H-NMR (200 MHz, CD$_3$OD): 1.25-1.4 (m; 8H), 1.5-1.7 (m; 4H), 2.23 (t; J=7.31 Hz; 2H), 2.87 (t; J=7.45 Hz; 2H).

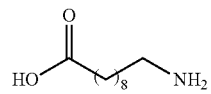

10-Aminodecanoic Acid (8b)—

10-bromodecanoic acid (2.51 gr, 10 mmol) was added to a round bottom flask containing 80 mL of aqueous ammonium hydroxide (25% NH$_3$). The resulting mixture was stirred for 24 hours at room temperature, after which the aqueous solution was evaporated under reduced pressure, resulting in 8b as a white solid at quantitative yield. $^1$H-NMR (200 MHz, CD$_3$OD): 1.25-1.4 (m; 10H), 1.5-1.7 (m; 4H), 2.15 (t; J=7.38 Hz; 2H), 2.89 (t; J=7.48 Hz; 2H).

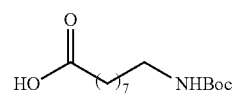

9-(Tert-Butoxycarbonylamino)Nonanoic Acid (9a)—

9-aminononanoic acid (8.46 mmol) was Boc-protected as described above, resulting in 7.26 mmol of clean product at 86% yield. $^1$H-NMR (200 MHz, CDCl$_3$): 1.25-1.7 (m; 21H), 2.30 (t; J=7.4 Hz, 2H), 3.05 (t; J=6.8 Hz, 2H), 4.53 (s, 1H).

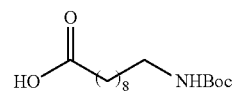

10-(Tert-Butoxycarbonylamino)Decanoic Acid (9b)—

10-aminodecanoic acid (5.57 mmol) was Boc-protected as described above, resulting in 4.27 mmol of clean product at 77% yield. $^1$H-NMR (200 MHz, CDCl$_3$): 1.25-1.7 (m; 23H), 2.34 (t; J=7.33 Hz, 2H), 3.07 (t; J=6.25 Hz, 2H), 4.53 (s, 1H).

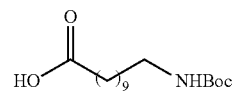

11-(Tert-Butoxycarbonylamino)Undecanoic Acid (9c)—

11-aminoundecanoic acid (18.55 mmol) was Boc-protected as described above, resulting in 17.4 mmol of clean product at 98% yield. $^1$H-NMR (200 MHz, CDCl$_3$): 1.25-1.7 (m; 25H), 2.34 (t; J=7.35 Hz, 2H), 3.1 (t; J=6.2 Hz, 2H), 4.52 (s, 1H).

General Procedure for Coupling of Homoserine Lactone, Using Meldrums Acid:

N-(dimethylamino)pyridine (DMAP) (0.257 gr, 2.1 mmol), N,N-dicyclohexylcarbodiimide (DCC) (0.454 gr, 2.2 mmol), the desired alkyl carboxylic acid (2 mmol) and Meldrum's acid (0.288 gr, 2 mmol) were dissolved in 20 mL of dichloromethane. The resulting solution was stirred overnight and then filtered to remove N,N-dicyclohexyl urea formed in the reaction. The filtrate was concentrated in vacuo. The resulting residue was dissolved in DMF (15 mL) and α-amino-γ-butyrolactone hydrobromide (0.364 gr, 2 mmol) was added. The mixture was stirred at room temperature for 1 hour and at 60° C. for 4 additional hours. The resulting solution was diluted with ethyl acetate 50 mL, and washed with saturated sodium bicarbonate solution, 1 M sodium hydrogen sulfate solution and brine. The organic phase was dried over magnesium sulfate, filtered and concentrated in vacuo. Further purification was done by flash chromatography.

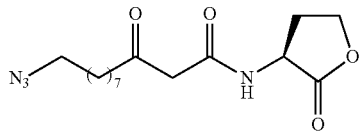

11-azido-3-oxo-N-(2-oxotetrahydrofuran-3-yl)undecanamide (6a)

Product 5a was reacted with Meldrum's acid as described above, and the resulting crude mixture was purified by column chromatography to afford product 6a at 66% yield.

$^1$H-NMR (200 MHz, CDCl$_3$): 1.2-1.4 (m; 8H), 1.5-1.7 (m; 4H), 2.1-2.3 (m; 1H), 2.51 (t; J=7.3; 2H), 2.6-2.75 (m; 1H), 3.21 (t; J=6.85 Hz; 2H), 3.44 (s; 2H), 4.2-4.3 (m; 1H), 4.4 (dt; J$_1$=9 Hz, J$_2$=1.4 Hz; 1H), 4.5-4.65 (m; 1H), 7.7 (d; J=6.6 Hz; 1H).

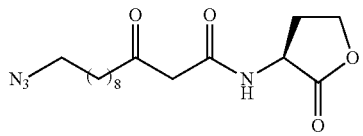

12-azido-3-oxo-N-(2-oxotetrahydrofuran-3-yl)dodecanamide (6b)

Product 5b was reacted with Meldrum's acid as described above, the resulting crude mixture was purified by column chromatography to yield product 6b in total yield of 38%
$^1$H-NMR (200 MHz, CDCl$_3$): 1.2-1.4 (m; 10H), 1.5-1.7 (m; 4H), 2.1-2.3 (m; 1H), 2.50 (t; J=7.2 Hz; 2H), 2.6-2.75 (m; 1H), 3.20 (t; J=6.85 Hz; 2H), 3.44 (s; 2H), 4.2-4.3 (m; 1H), 4.4 (dt; J$_1$=9 Hz, J$_2$=1.4 Hz; 1H), 4.5-4.7 (m; 1H), 7.75 (d; J=6.7; 1H).

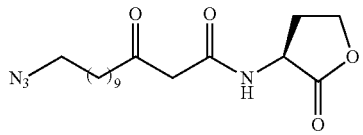

13-azido-3-oxo-N-(2-oxotetrahydrofuran-3-yl)tridecanamide (6c)

Product 5c was reacted with Meldrum's acid as described above, the resulting crude mixture was purified by column chromatography to afford product 6c at 66% yield. $^1$H-NMR (200 MHz, CDCl$_3$): 1.2-1.4 (m; 12H), 1.5-1.7 (m; 4H), 2.1-2.3 (m; 1H), 2.52 (t; J=7.3 Hz; 2H), 2.6-2.8 (m; 1H), 3.24 (t; J=6.8 Hz; 2H), 3.46 (s; 2H), 4.2-4.3 (m; 1H), 4.4 (dt; J$_1$=9 Hz, J$_2$=1.4 Hz; 1H), 4.5-4.65 (m; 1H), 7.85 (d; J=6.9; 1H).

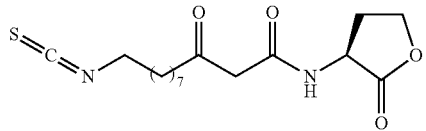

11-isothiocyanato-3-oxo-N-(2-oxotetrahydrofuran-3-yl)undecanamide (7a, itc-11)

To a solution of 6a (0.24 mmol) in toluene (10 mL), triphenyl phosphine (69 mg, 0.26 mmol) was added in one portion at room temperature. The solution was heated to 50° C. and stirred for one hour. After cooling the solution to room temperature, carbon disulfide (30 μL, 0.48 mmol) was added dropwise. The solution was then heated back to 50° C. and stirred for additional two hours. The crude mixture was concentrated in vacuo and purified by column chromatography to yield 7a at 93%. $^1$H-NMR (500 MHz, CDCl$_3$): 1.22-1.31 (m; 6H), 1.32-1.4 (m; 2H), 1.52-1.57 (m; 2H), 1.62-1.68 (m; 2H), 2.3-2.3 (m; 1H), 2.52 (t; J=7.3 Hz; 2H), 2.66-2.72 (m; 1H), 3.45 (s; 2H), 3.48 (t; J=6.82 Hz; 2H), 4.22-4.28 (m; 1H), 4.45 (t; J=8.9 Hz; 1H), 4.52-4.61 (m; 1H), 7.7 (d; J=6.3; 1H). $^{13}$C-NMR (500 MHz, CDCl$_3$): 23.2, 26.4, 28.5, 28.7, 29.1, 29.5, 29.8, 43.7, 45.0, 48.4, 49.0, 66.0, 129.3, 166.6, 175.1, 206.4. MS (ESI) m/z: calcd: [M$^+$] 341.2, measured: [M$^+$] 341.06.

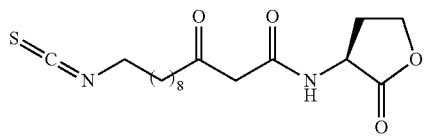

12-isothiocyanato-3-oxo-N-(2-oxotetrahydrofuran-3-yl)dodecanamide (7b, itc-12)

To a solution of 6b (0.24 mmol) in toluene 10 mL, triphenyl phosphine (69 mg, 0.26 mmol) was added at one portion in room temperature. The solution was heated to 50° C. and stirred for one hour. After cooling the solution to room temperature, carbon disulfide (30 μL, 0.48 mmol) was added dropwise. The solution was then heated back to 50° C. and stirred for additional two hours. The crude mixture was concentrated in vacuo and purified by column chromatography to yield 7b at 66%. $^1$H-NMR (500 MHz, CDCl$_3$): 1.25-1.32 (m; 8H), 1.33-1.41 (m; 2H), 1.53-1.59 (m; 2H), 1.64-1.7 (m; 2H), 2.2-2.28 (m; 1H), 2.52 (t; J=7.3 Hz; 2H), 2.7-2.76 (m; 1H), 3.46 (s; 2H), 3.49 (t; J=6.82 Hz; 2H), 4.24-4.3 (m; 1H), 4.46 (t; J=8.9 Hz; 1H), 4.55-4.61 (m; 1H), 7.6 (d; J=6.3 Hz; 1H). $^{13}$C-NMR (500 MHz, CDCl$_3$): 23.2, 26.4, 28.6, 28.8, 29.1, 29.7, 29.8, 43.8, 45.0, 48.2, 49.0, 65.9, 129.3, 166.4, 174.9, 206.5. MS (ESI) m/z: calcd: [M$^+$] 355.1, measured: [M$^+$] 355.05.

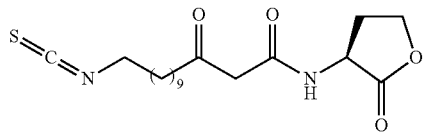

13-isothiocyanato-3-oxo-N-(2-oxotetrahydrofuran-3-yl)tridecanamide (7c, itc-13)

To a solution of 6c (0.24 mmol) in toluene 10 mL, triphenyl phosphine (69 mg, 0.26 mmol) was added at one portion in room temperature. The solution was heated to 50° C. and stirred for one hour. After cooling the solution to room temperature, carbon disulfide (30 μL, 0.48 mmol) was added dropwise. The solution was then heated back to 50° C. and stirred for additional two hours. The crude mixture was concentrated in vacuo and purified by column chromatography to yield 7c at 57%. $^1$H-NMR (500 MHz, CDCl$_3$): 1.22-1.30 (m; 10H), 1.34-1.40 (m; 2H), 1.51-1.58 (m; 2H), 1.63-1.7 (m; 2H), 2.2-2.28 (m; 1H), 2.51 (t; J=7.35 Hz; 2H), 2.67-2.73 (m; 1H), 3.45 (s; 2H), 3.48 (t; J=6.66 Hz; 2H), 4.22-4.28 (m; 1H), 4.45 (t; J=8.97 Hz; 1H), 4.55-4.61 (m; 1H), 7.7 (d; J=6.3 Hz; 1H). $^{13}$C-NMR (500 MHz, CDCl$_3$): 23.2, 26.5, 28.7, 28.9, 29.2, 29.5, 29.8, 43.7, 45.0, 48.3, 49.0, 65.9, 129.3, 166.5, 175.0, 206.5. MS (ESI) m/z: calcd: [M$^+$] 367.2, measured: [M$^+$] 369.06

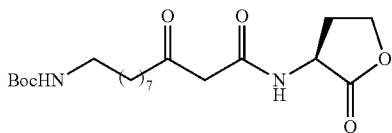

tert-butyl 9,11-dioxo-11-(2-oxotetrahydrofuran-3 ylamino)-undecylcarbamate (10a)

Product 9a was reacted with Meldrum's acid as described above, and the resulting crude mixture was purified by column chromatography to yield product 10a at 36%. $^1$H-NMR (200 MHz, CDCl$_3$): 1.24-1.32 (m; 10H), 1.27 (s; 9H), 1.58-1.7 (m; 2H), 2.10-2.29 (br s; 1H), 2.52 (t; J=7.31; 2H), 2.62-2.80 (br s; 1H), 3.07 (t; J=6.90 Hz; 2H), 3.46 (s; 2H), 4.23-4.34 (m; 1H), 4.46 (dt; J$_1$=9.15, J$_2$=0.9; 1H), 4.54-4.64 (m; 1H), 7.7 (d; J=4.81; 1H).

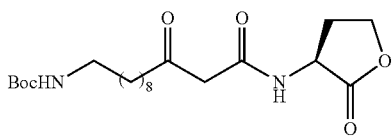

tert-butyl 10,12-dioxo-12-(2-oxotetrahydrofuran-3 ylamino)-dodecylcarbamate (10b)

Product 9b was reacted with Meldrum's acid as described above, and the resulting crude mixture was purified by column chromatography to yield product 10b at 32%. $^1$H-NMR (200 MHz, CDCl$_3$): 1.24-1.32 (m; 12H), 1.43 (s; 9H), 1.5-1.62 (m; 2H), 2.10-2.30 (br s; 1H), 2.52 (t; J=7.27 Hz; 2H), 2.66-2.82 (br s; 1H), 3.07 (t; J=6.91 Hz; 2H), 3.46 (s; 2H), 4.22-4.34 (m; 1H), 4.47 (dt; J$_1$=9.15 Hz, J$_2$=1.4 Hz; 1H), 4.54-4.64 (m; 1H), 7.6 (d; J=4.84 Hz; 1H).

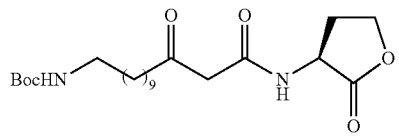

tert-butyl 11,13-dioxo-13-(2-oxotetrahydrofuran-3 ylamino)-tridecylcarbamate (10c)

Product 9c was reacted with Meldrum's acid as described above, and the resulting crude mixture was purified by column chromatography to yield product 10c at 59%. $^1$H-NMR (200 MHz, CDCl$_3$): 1.22-1.32 (m; 14H), 1.43 (s; 9H), 1.53-1.62 (m; 2H), 2.10-2.30 (br s; 1H), 2.51 (t; J=7.27 Hz; 2H), 2.66-2.8 (br; 1H), 3.08 (t; J=6.91 Hz; 2H), 3.45 (s; 2H), 4.22-4.33 (m; 1H), 4.46 (dt; J$_1$=9.16 Hz, J$_2$=0.56 Hz; 1H), 4.54-4.64 (m; 1H), 7.7 (d; J=4.93; 1H).

General Procedure for Products 11a-g:

Compounds 10a-c (0.705 mmol) were dissolved in dichloromethane 4 mL. Trifluoroacetic acid (4 mL) was added in one portion and the resulting solution was stirred at room temperature for 20 minutes, after which the Boc moiety was fully removed (confirmed by NMR). The solvent was evaporated and dichloromethane (5 mL) was added to the resulting residue. The pH was adjusted to ~7 by adding triethylamine, and pyridine (62 μL, 0.785 mmol) was added. The reaction mixture was cooled to 0° C. on an ice bath and a solution of bromoacetyl bromide (64 μL, 0.74 mmol) in dichloromethane (4.5 mL) (for products 11 d-g chloroacetyl chloride was used) was added dropwise over a period of 5 minutes. The reaction mixture was kept on ice for 1 hour, after which it was diluted with saturated sodium bicarbonate solution (100 mL) and extracted with chloroform (3×30 mL). The organic phases where combined, washed with brine, dried over magnesium sulfate, filtered and concentrated in vacuo. The final products (11a-g) were purified by RP-HPLC.

11a (hal-11-Br)—

$^1$H-NMR (500 MHz, CDCl$_3$): 1.22-1.32 (br; 8H), 1.51 (t; J=6.81 Hz; 2H), 1.56 (t; J=6.78 Hz; 2H), 2.18-2.28 (m; 1H), 2.51 (t; J=7.25 Hz; 2H), 2.7-2.76 (m, 1H), 3.25 (q; J=6.71 Hz: 2H), 3.45 (s; 2H), 3.86 (s; 2H), 4.22-4.29 (m; 1H), 4.46 (t, J=8.93 Hz; 1H), 4.55-4.61 (m; 1H), 6.49 (br, 1H), 7.67 (br; 1H). $^{13}$C-NMR (500 MHz, CDCl$_3$): 23.20, 26.56, 28.74, 28.85, 29.04, 29.16, 29.34, 29.86, 40.20, 43.81, 48.14, 49.08, 65.91, 165.38, 166.39, 174.78, 206.51. MS (ESI) m/z: calcd: [M$^+$] 419.3, measured: [M$^+$] 419.04.

11b (hal-12-Br)—

$^1$H-NMR (500 MHz, CDCl$_3$): 1.23-1.31 (br; 10H), 1.51 (t; J=7.13 Hz; 2H), 1.55 (t; J=7.31 Hz; 2H), 2.18-2.28 (m; 1H), 2.51 (t; J=7.33 Hz; 2H), 2.69-2.75 (m, 1H), 3.25 (q; J=6.75 Hz: 2H), 3.45 (s; 2H), 3.86 (s; 2H), 4.23-4.29 (m; 1H), 4.45 (dt, J$_1$=9.08 Hz, J$_2$=1.44 Hz; 1H), 4.55-4.61 (m; 1H), 6.54 (br, 1H), 7.73 (d; J=6.47 Hz; 1H). $^{13}$C-NMR (500 MHz, CDCl$_3$): 23.24, 26.67, 28.83, 29.02, 29.13, 29.39, 29.70, 40.21, 43.77, 48.30, 49.04, 65.93, 165.39, 166.48, 174.92, 206.47. MS (ESI) m/z: calcd: [M$^+$] 433.3, measured: [M$^+$] 435.03.

11c (hal-13-Br)—

$^1$H-NMR (500 MHz, CDCl$_3$): 1.22-1.32 (br; 12H), 1.52 (t; J=7.02 Hz; 2H), 1.57 (t; J=7.03 Hz; 2H), 2.18-2.28 (m; 1H), 2.52 (t; J=7.34 Hz; 2H), 2.71-2.78 (m, 1H), 3.27 (q; J=6.75 Hz: 2H), 3.46 (s; 2H), 3.87 (s; 2H), 4.23-4.30 (m; 1H), 4.47 (dt, J$_1$=9.07 Hz, J$_2$=1.27 Hz; 1H), 4.55-4.61 (m; 1H), 6.51 (br, 1H), 7.70 (d; J=5.76 Hz; 1H). $^{13}$C-NMR (500 MHz, CDCl$_3$): 23.29, 26.73, 28.88, 29.11, 29.21, 29.30, 29.40, 29.82, 40.26, 43.87, 48.12, 49.06, 65.89, 165.30, 166.39, 174.79, 206.54. MS (ESI) m/z: calcd: [M⁺] 447.1, measured: [M⁺] 447.17.

11d (hal-11-Cl)—

$^1$H-NMR (500 MHz, CDCl$_3$): 1.25-1.33 (br; 10H), 1.5-1.59 (br; 4H), 2.19-2.29 (m; 1H), 2.52 (t; J=7.29 Hz; 2H), 2.70-2.76 (m, 1H), 3.28 (q; J=6.75 Hz; 2H), 3.46 (s; 2H), 4.04 (s; 2H), 4.24-4.30 (m; 1H), 4.47 (t, J$_1$=9.00 Hz; 1H), 4.56-4.62 (m; 1H), 6.61 (br, 1H), 7.72 (br; 1H). $^{13}$C-NMR (500 MHz, CDCl$_3$): 23.17, 26.59, 28.72, 28.84, 29.03, 29.19, 29.69, 39.80, 42.67, 43.69, 48.25, 49.02, 65.88, 165.83, 166.42, 174.85, 206.37. MS (ESI) m/z: calcd: [M⁺] 375.8, measured: [M⁺] 375.07.

11e (hal-12-Cl)—

$^1$H-NMR (500 MHz, CDCl$_3$): 1.22-1.30 (br; 12H), 1.48-1.58 (br; 4H), 2.17-2.27 (m; 1H), 2.50 (t; J=7.35 Hz; 2H), 2.68-2.75 (m, 1H), 3.26 (q; J=6.78 Hz; 2H), 3.44 (s; 2H), 4.02 (s; 2H), 4.22-4.29 (m; 1H), 4.45 (dt, J$_1$=9.06 Hz, J$_2$=1.30 Hz; 1H), 4.54-4.61 (m; 1H), 6.58 (br, 1H), 7.71 (d; J=6.20 Hz; 1H). $^{13}$C-NMR (500 MHz, CDCl$_3$): 23.25, 26.71, 28.86, 29.08, 29.19, 29.70, 39.85, 42.67, 43.78, 48.22, 48.99, 65.87, 165.77, 166.40, 174.85, 206.46. MS (ESI) m/z: calcd: [M⁺] 388.9, measured: [M⁺] 389.1.

11g (hal-13-Cl)—

$^1$H-NMR (500 MHz, CDCl$_3$): 1.22-1.30 (br; 12H), 1.48-1.58 (br; 4H), 2.17-2.27 (m; 1H), 2.50 (t; J=7.35 Hz; 2H), 2.68-2.75 (m, 1H), 3.26 (q; J=6.78 Hz; 2H), 3.44 (s; 2H), 4.02 (s; 2H), 4.22-4.29 (m; 1H), 4.45 (dt, J$_1$=9.06, J$_2$=1.30; 1H), 4.54-4.61 (m; 1H), 6.58 (br, 1H), 7.71 (d; J=6.20; 1H). $^{13}$C-NMR (500 MHz, CDCl$_3$): 23.25, 26.71, 28.86, 29.08, 29.19, 29.70, 39.85, 42.67, 43.78, 48.22, 48.99, 65.87, 165.77, 166.40, 174.85, 206.46. MS (ESI) m/z: calcd: [M⁺] 402.9, measured: [M⁺] 403.08.

FIG. 3D shows the 1H-NMR and 13C-NMR analysis results for compound 7a (above).

FIG. 3E shows the 1H-NMR and 13C-NMR analysis results for compound 7b (above).

FIG. 3F shows the 1H-NMR and 13C-NMR analysis results for compound 7c (above).

FIG. 3G shows 13C-DEPT-NMR and 2D COSY NMR analysis results for compound 7c (above).

These results are shown as non-limiting examples only of some of the data obtained from analysis of the above compounds.

Example 2

Inhibition of Bacterial Communication by Compounds of Example I

Materials and Methods

Chemical Synthesis.

Syntheses of isothiocyanates itc-11,12,13 and haloacetamides hal-11,12,13-Br & hal-11,12,13-Cl were performed as described above.

Mass Spectrometry.

All MS analyses were performed on a LCQ Fleet mass spectrometer (Thermo Scientific) with an ESI source. Spectra were collected in positive ion mode and analyzed by Xcalibur and Promass software (Thermo Scientific). For LC/MS analyses a Surveyor Plus HPLC System (Thermo Scientific) was used, equipped with a Luna C18, 5 μm (150×4.6 mm) column at a flow rate of 0.5 mL/min, using a mobile phase linear gradient of 0.1% aqueous formic acid (solvent A) and CH$_3$CN containing 0.1% formic acid (solvent B).

Expression of LasR-LBD.

The expression of full length LasR was previously found to yield largely insoluble protein in the presence or absence of the native ligand, 3-oxo-C$_{12}$-HSL (Bottomley, M. J., Muraglia, E., Bazzo, R. & Carfi, A. Molecular insights into quorum sensing in the human pathogen Pseudomonas aeruginosa from the structure of the virulence regulator LasR bound to its autoinducer. J Biol Chem 282, 13592-600 (2007)). Therefore, expression was performed using a strain transformed with a pETM-11 vector encoding for a shortened, His$_6$-tagged LasR construct, LasR-LBD (ligand-binding domain), spanning residues Met-1 to Lys-173. The plasmid was transferred into E. coli BL21 and cells were incubated in 1 mL rich LB medium for 1 hour. The cells were then grown on LB agar plates containing kanamycin (50 micro-g/mL). For expression, a single colony was selected and transferred into 5 mL of rich LB medium containing kanamycin and grown overnight. Proteins were expressed in the presence of either native 3-oxo-C$_{12}$-HSL or different inhibitors and purified by Ni$^{2+}$ affinity chromatography as previously described (Bottomley, M. J., Muraglia, E., Bazzo, R. & Carfi, A. Molecular insights into quorum sensing in the human pathogen Pseudomonas aeruginosa from the structure of the virulence regulator LasR bound to its autoinducer. J Biol Chem 282, 13592-600 (2007), yielding ~70 mg of purified protein per liter of LB medium using large scale expression conditions, and ~0.5-1 mg of purified protein from 50 mL of LB medium using small scale expression conditions. The purification process was monitored by SDS-PAGE electrophoresis and the molecular mass of the purified proteins was confirmed by mass spectrometry.

Large Scale Expression:

1 mL of the overnight grown cell culture was used to inoculate 1 liter of rich LB medium containing kanamycin (50 micro-g/mL) and 10-100 micro-M of 3-oxo-C$_{12}$-HSL or inhibitors 7a-c and 11a-g. Cells were grown to an optical density (OD$_{600\,nm}$) of 0.4, after which expression was induced at 21° C. by addition of 0.2 mM isopropyl 1-thio-beta-D-galactopyranoside (IPTG) and an additional amount of ligand/inhibitor was added to the media. After reaching an OD$_{600\,nm}$ of 1.4 (approx. 6-8 hours), cells were centrifuged at 6000 rpm, washed and resuspended in lysis buffer containing 5 mM imidazole, 300 mM NaCl, 50 mM Tris-HCl, pH 8. Cells were ultrasonicated for 2 minutes at 70% amplitude for two cycles. The lysate was centrifuged at 12,000 rpm for 30 minutes, and the supernatants were purified by Ni$^{2+}$ affinity chromatography.

Small scale expression was performed in 50 mL volume following the previous procedure. Cells were harvested by chemical lysis, adding 1 mL of lysis buffer (5 mM imidazole, 300 mM NaCl, 0.2% (v/v) Triton X-100, 0.75 μg/mL DNase-I, 0.05 mM MgCl$_2$, 0.01 mM CaCl$_2$, 50 mM Tris-HCl, pH 8, and 0.01% (v/v) protein inhibitor cocktail), and incubated for 60 minutes at 37° C. Cell debris was removed by centrifugation at 4,000 rpm for 15 minutes. The supernatants were purified using Ni-NTA spin columns (QIAGEN).

P. aeruginosa Wild-Type Strain (PA01) QS Inhibition Assay.

The P. aeruginosa PA01 wild type strain harboring plasmid pKD201 containing a LasI reporter coupled to the luxCD-ABE luminescence system (Duan, K. & Surette, M. G. Environmental regulation of Pseudomonas aeruginosa PAO1 Las and Rhl quorum-sensing systems. J Bacteriol 189, 4827-36 (2007)), was incubated overnight in LB medium containing 300 micro-g/ml of trimethoprim. A 96-well black microtiter plate (Greiner) was prepared with the desired concentrations of inhibitors (up to 1 mM, above which growth inhibition was observed), and bacteria were added to reach a final absorbance density (OD$_{600\,nm}$) of 0.015. The plate was then incubated for a period of 12 hours at 37° C. During this time, luminescence measurements were performed at 10 minute intervals. The relative luminescence was then plotted against the added inhibitor concentration; $IC_{50}$ values were calculated using Grafit 6.0 (Erithacus Software).

P. aeruginosa PAO-JP2 QS Agonist/Antagonist Assay.

PAO-JP2, a lasI/rhlI-deleted strain harboring plasmid pKD201 containing a LasI reporter coupled to the luxCD-ABE luminescence system (see above), was incubated overnight in LB medium containing 300 micro-g/ml of trimethoprim. A 96-well black microtiter plate (Greiner) was prepared as described for the PA01 inhibition assay. The relative luminescence was then plotted against the added inhibitor concentration; $IC_{50}$ values were calculated using Grafit 6.0 (Erithacus Software). For antagonist experiments, a final concentration of 50 nM 3-oxo-$C_{12}$-HSL was used.

E. coli DH5-Alpha LasR Agonist/Antagonist Assay.

E. coli DH5-alpha harboring the LasR expression vector. pJN105L, and a plasmid-borne PlasI-lacZ fusion (pSC11) (Lee, J. H., Lequette, Y. & Greenberg, E. P. Activity of purified QscR, a Pseudomonas aeruginosa orphan quorum-sensing transcription factor. Mol Microbiol 59, 602-9 (2006)) was used to quantify quorum sensing inhibition by measuring expression levels of beta-galactosidase. Bacteria were incubated overnight in LB medium containing 100 micro-g/mL of ampicillin and 15 micro-g/mL of gentamicin. The culture was diluted at a 1:10 ratio by volume with fresh medium and further incubated until an $OD_{600\,nm}$ of 0.3 was reached. A 96 well microtiter plate (Greiner) was prepared with the desired concentrations of inhibitors and bacteria were added to reach a final absorbance density ($OD_{600\,nm}$) of 0.3. Expression was induced at the edition of L-(+)-arabinose (4 mg/mL) and the plates were incubated at 37° C. for a period of 4 hours ($OD_{600\,nm}$ of 0.45-0.5). The cultures were then assayed for beta-galactosidase activity according to the Miller assay method[46]: 200 mL aliquots were transferred to clear 96-well microtiter plates and the $OD_{600}$ was recorded. 100 mL of each well was then added to a polypropylene-based 96-well microtiter plate containing 200 mL Z-Buffer, 10 mL chloroform and 5 mL of 0.1% SDS (w/v). Wells were thoroughly rinsed by pipetation, after which the chloroform was allowed to settle. 100 mL of the aqueous upper layer was transferred to a fresh 96-well microtiter plate and 20 mL of ortho-nitrophenyl-beta-D-galactopyranoside (ONPG, 4 mg/mL in phosphate buffer of pH 7) were added. The plates were incubated 35 minutes at 28° C. The reaction was terminated with the addition of 80 mL of 1 M sodium carbonate solution, and absorption at two wavelengths (550 nm, 429 nm) was recorded. Miller units were calculated using standard methods (Miller, J. H. Experiments in Molecular Genetics. 352-355 (Cold Spring Harbor Laboratories, 1972)). For antagonist experiments, a final concentration of 50 nM 3-oxo-$C_{12}$-HSL was used.

Trypsin Digestion of LasR-LBD and LasR-LBD-itc-11/12—

Trypsin (Promega industries) was dissolved in 50 mM Tris buffer (pH=8) containing 0.1% SDS, 3 mM β-mercaptoethanol and 10% acetonitrile, in a 1:100 enzyme:LasR mass ratio. The desired amount of LasR was added and the solution was incubated for 2 hours at 37° C. Trypsin was deactivated by storing the mixture at −20° C. Samples were analyzed by LC-MS and desired peaks were subjected to $MS^2$ for sequencing as described below.

| Cyc-containing fragment | Rt (min) | Calculated mass [Da] | Found mass $[Da][M^{+2}]$ | Found mass $[Da][M^{+3}]$ | Found mass $[Da][M^{+4}]$ |
|---|---|---|---|---|---|
| Native LasR-LBD | 10.37 | 2903.44 | 1452.75 | 968.92 | 726.45 |
| LasR-itc-12 | 11.44 | 3257.94 | 1630.05 | 1087.00 | 815.81 |
| LasR-itc-11 | 11.21 | 3243.44 | 1623.03 | 1082.14 | 811.81 |

Structural Analysis and Modeling of Interactions with QS Inhibitors.

Protein-ligand images were prepared with PyMOL. For modeling the LasR-LBD-QSI interactions, hydrogen atoms were added to LasR to simulate a pH of 7.4. The positions of these hydrogens and of the protein side chains were optimized by energy minimization (5000 steepest descent steps), using the Merck molecular force field (MMFF-S) as implemented in Macromodel version 9.0 (Schrödinger LLC software), keeping first the protein backbone and then the AHL structure rigid.

Results

Figure 4:
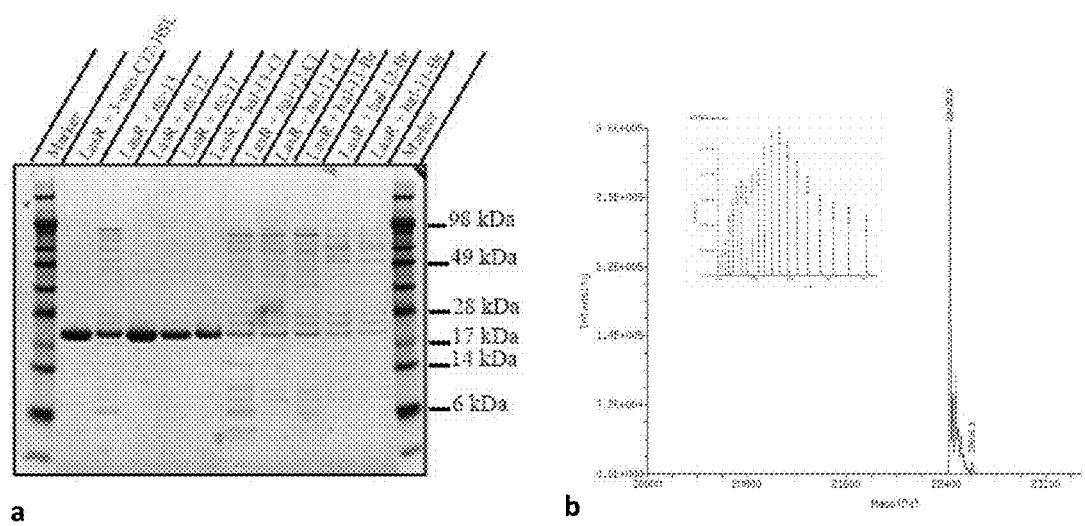
FIG. 4 shows covalent binding of itc-11 and itc-12 to LasR-LBD; a) SDS-PAGE of purified LasR-LBD, expressed in the presence of 3-oxo-$C_{12}$-HSL and nine reactive probes; b) deconvoluted mass spectrum of LasR-LBD expressed in the presence of 3-oxo-$C_{12}$-HSL; c) deconvoluted MS of LasR-LBD expressed in the presence of itc-11; d) deconvoluted MS of LasR-LBD expressed in the presence of itc-12. Insets show spectral data before deconvolution.
Figure 4:
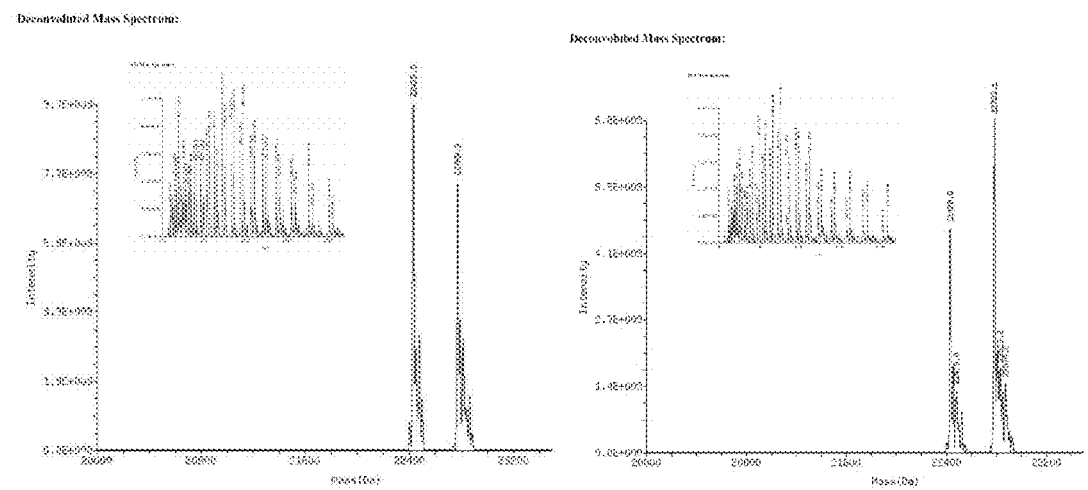

Upon incubation of bacteria expressing LasR with some non-limiting examples of the compounds of formula I (specifically the haloacetamide compounds of Formula I as shown for example in FIG. 2), soluble LasR-LBD could be obtained (FIG. 4a). Importantly, in the absence of probe or 3-oxo-$C_{12}$-HSL, no soluble LasR-LBD was observed, while over-expression of LasR in the presence of most of the haloacetamides resulted in the appearance of only minor amounts of soluble LasR-LBD. Similarly, when cells were incubated with 4-Br-PHL, no soluble LasR was observed (data not shown), confirming the earlier findings of Bottomley et al (reference given above).

LC-MS measurements revealed that the purified LasR-LBD (MW 22,430 Da, FIG. 4b) could be covalently modified with itc-11 (MW 340 Da) and itc-12 (MW itc-12 354 Da) (FIG. 4c,d), with calculated masses being in good agreement with measured masses (22,770 Da vs 22,770 Da and 22,784 Da vs 22,783 Da, respectively). Importantly, even though a large excess of the exemplary compounds of Formula I was used (10-100 micro-M in the bacterial growth culture, leading to expression of 0.5-3.5 micro-M LasR-LBD), no more than one unit of covalently attached compound could be observed, indicating the reaction to be sufficiently specific at the concentrations used. No such covalent modifications were observed upon purification of LasR-LBD from cells incubated with any of the haloacetamides. From these results, but without wishing to be limited by a single hypothesis, it is possible that either no covalent reaction had taken place between the haloacetamides and LasR, meaning that their inhibitory effect is mediated in a manner similar to other strong non-covalent inhibitors (i.e. binding nascent LasR followed by misfolding and precipitation), or that a covalent reaction had occurred, yet, due to the insolubility of the protein, it was not possible to observe the product.

Covalent Inhibitory Compounds of Formula I React Specifically with Cys79 in the LasR Binding Pocket LasR-LBD was expressed in the presence of either 3-oxo-$C_{12}$-HSL or itc-12 (or itc-11), followed by protein purification and trypsin digestion. The cysteine-containing fragment (72-VDPTVSHCTQSVLPIFWEPSIYQTR-96) was identified by LC-MS as a single peak (2903.4 Da), while a modified peptide with increased retention time and a mass gain corresponding to itc-12 (or itc-11) attachment was also identified (data not shown). Tandem MS/MS measurements on both modified and unmodified LasR-LBD confirmed that indeed Cys79 had reacted with the covalent probes (data not shown).

In addition, two point mutations (Cys→Ala or Cys→Ser) were introduced to the native protein to examine whether LasR-LBD is still covalently modified in the absence of a reactive thiol moiety in its binding pocket. As expected, upon over-expression of the LasR-LBD Cys79Ala mutant in bacteria incubated with itc-12, no covalent modification was detected (data not shown). Soluble protein was, however, obtained, indicating that the mutant LasR was able to recognize the isothiocyanate probe as a substrate that induces correct folding. Likewise, the Cys79Ser mutation yielded expression of soluble protein in the presence of itc-12, despite no covalent modification being observed.

Notably, when native LasR-LBD was expressed in the presence of itc-11 and itc-12, covalent labeling often appeared incomplete and resulted in significant amounts of soluble, non-labeled LasR-LBD (25-40%, depending on conditions), indicating that an alternative binding mode for the isothiocyanates may exist in which the reactive carbon atom is located sufficiently far from Cys79 so as to prevent a reaction.

Computational Analysis of LasR-Isothiocyanate Interactions

Figure 5:
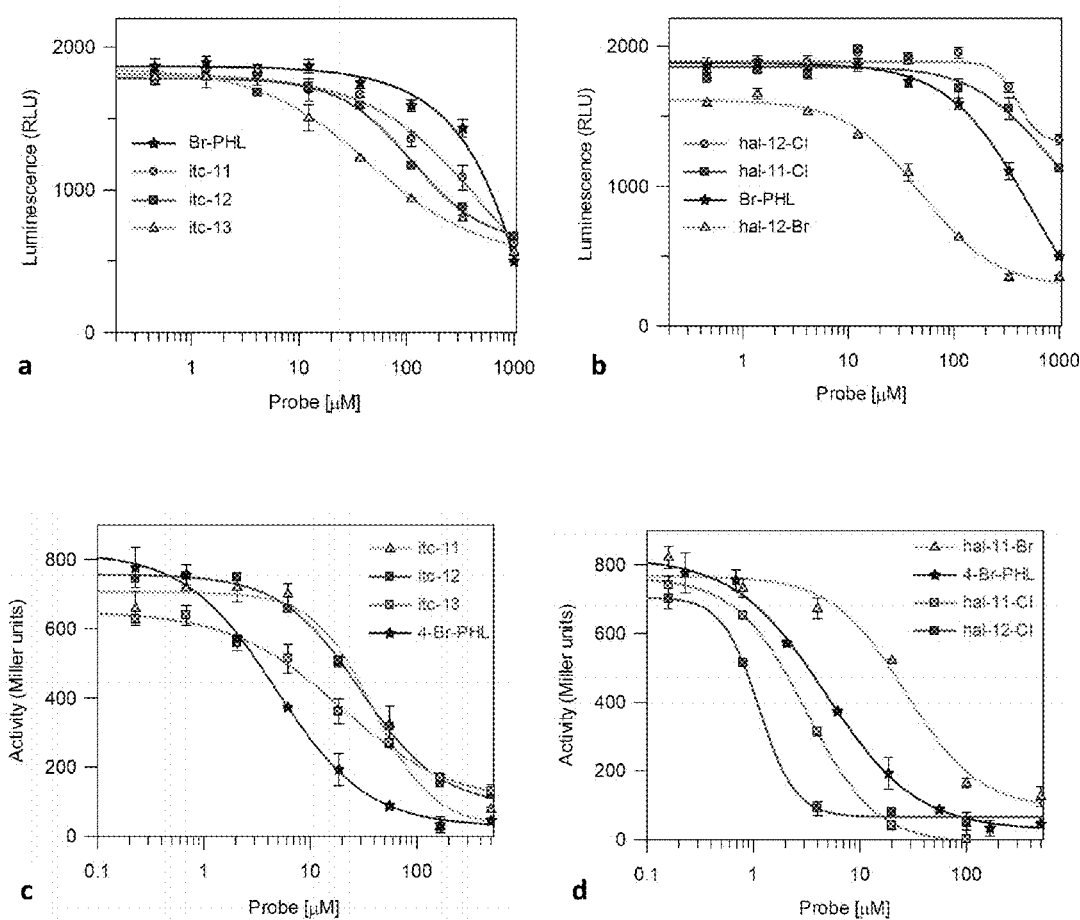
FIG. 5 Reporter gene assays. PAO1 QS inhibition by isothiocyanates (a) and haloacetamides (b); antagonism of LasR activation by 50 nM 3-oxo-$C_{12}$-HSL in *E. coli* (this reporter strain does not produce 3-oxo-$C_{12}$-HSL) by isothiocyanates (c) and haloacetamides (d). Each point represents the average of three experiments±SD.

To complement the above experimental data, computational conformational analyses and docking calculations simulating the binding of the isothiocyanates to LasR were performed. As a control to validate the docking procedure, the natural 3-oxo-$C_{12}$-HSL ligand was removed from its binding site and successfully re-docked, i.e. the conformation corresponding to the ligand in the crystal structure was very highly ranked among the output poses, with an RMSD<0.2 Å for all non-hydrogen atoms. The three isothiocyanate compounds were then docked into the LasR-binding site. The most highly ranked pose for each ligand was then submitted to an extensive conformational analysis in the context of the protein, which was considered as a rigid body. This analysis revealed that the longest isothiocyanate, i.e. itc-13, cannot be accommodated in the binding site without disrupting the interactions of the polar head group with the protein. In contrast, the shorter compounds, namely itc-11 and itc-12, can be accommodated whilst maintaining all favourable polar interactions with the protein. Interestingly, the energy-minimized conformers observed for both itc-11 and itc-12 clustered into two groups, differing significantly only in the orientation of their isothiocyanate group (FIG. 5) One orientation presents an ideal pre-organization for nucleophilic attack by the sulfur atom of Cys79, whereas the other orientation is sub-optimal for this reaction. For itc-11, the conformer population was equally divided (50/50), whereas for itc-12, approximately 66% of the population adopted the conformation suitable for the reaction. The nucleophilic attack would be enhanced by re-orientation of the Cys79 side chain towards the itc compounds; the LasR crystal structure suggests this rotamer would be permitted.

Reactive Probes Inhibit QS in *P. aeruginosa*

Figure 6:
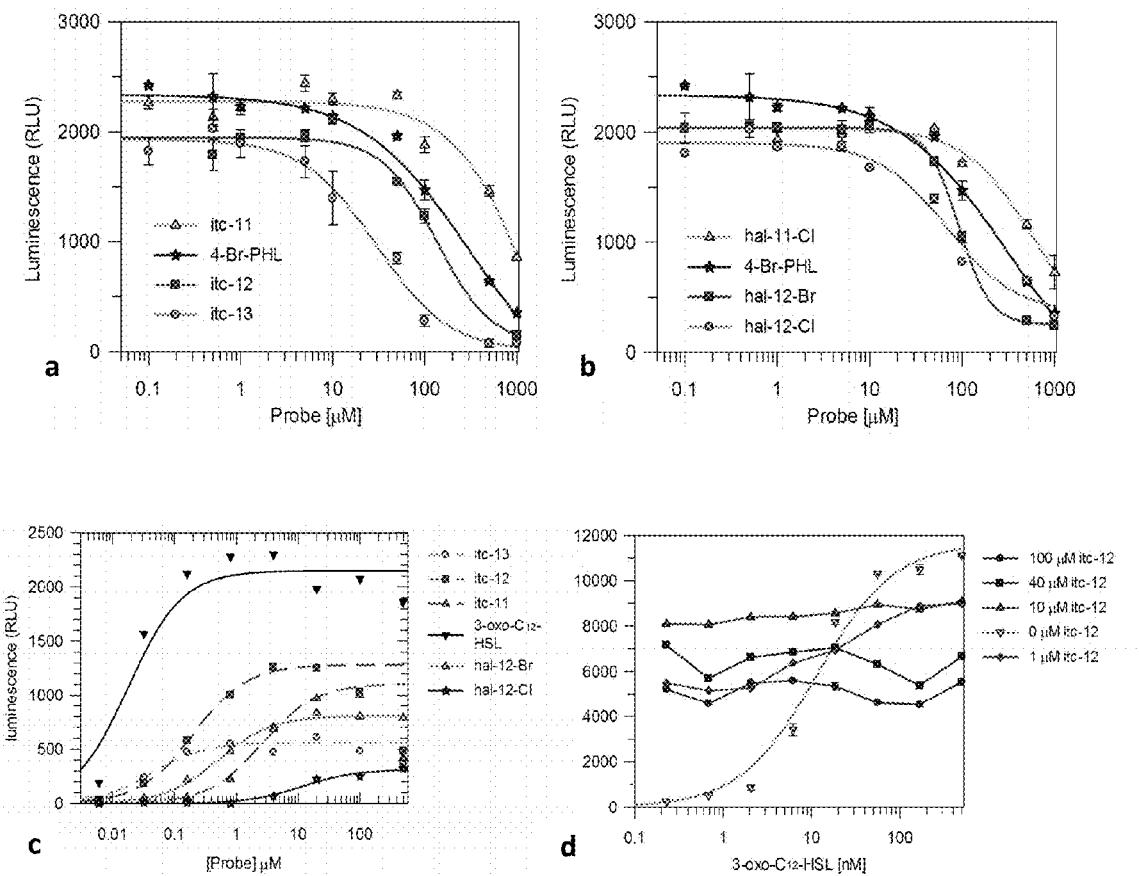
FIG. 6 PAO-JP2-based antagonist (a and b), agonist (c), and partial agonist (d) assays. The curve shapes in the partial agonist assay can be attributed to the covalent binding mode of itc-12, as detailed further in the Supplementary Information. Each point represents the average of three experiments±SD.

The activities of the covalent probes were evaluated using several reporter strains, namely the luminescent PAO1-luxABCDE wild type strain and a PAO1 lasI-rhlI double mutant (PAO-JP2-luxABCDE), as well as an *E. coli* β-galactosidase-LasR-based reporter strain. Several isothiocyanates and bromoacetamides strongly inhibited luminescense in the wild type strain (FIG. 6a,b), while some of the probes displayed both agonist and antagonist activity in assays performed with the PAO-JP2- and *E. coli* strains (FIG. 6c,d). To compare this data with those reported for known strong QS inhibitors, a control antagonist, 2-(4-bromophenyl)-N-(2-oxo-tetrahydrofuran-3-yl)-acetamide (4-Br-PHL), identified by Blackwell and co-workers as one of the most active *P. aeruginosa* QS antagonists (Geske, G. D., O'Neill, J. C., Miller, D. M., Mattmann, M. E. & Blackwell, H. E. Modulation of bacterial quorum sensing with synthetic ligands: systematic evaluation of N-acylated homoserine lactones in multiple species and new insights into their mechanisms of action. J Am Chem Soc 129, 13613-25 (2007)) was synthesized.

In the *E. coli*-based LasR antagonist studies (FIG. 6c,d), an $IC_{50}$ value for 4-Br-PHL (4.8±0.5 microM) was obtained that was similar to that reported by Geske et al. (3.9 micro-M; reference given above). Of the nine probes screened in these assays, the chloroacetamide, hal-12-Cl, appeared to be the best antagonist ($IC_{50}$: 1.1±0.1 micro-M), followed by hal-11-Cl and hal-11-Br ($IC_{50}$: 3.1±0.1 microM and 26.8±1.3 micro-M, respectively), and the three isothiocyanates, itc-11-13 ($IC_{50}$: 39.1±9.4, 29.8±0.5, 19.2±3.9 micro-M, respectively). Surprisingly, one of the bromoacetamides (i.e. hal-13-Br) showed a strong enhancement of LasR activation at higher concentrations in this assay, while its shorter analogs acted as strong inhibitors; without wishing to be limited by a single hypothesis, it is believed that the effect of hal-13Br is specific to this assay and in other situations this molecule would be inhibitory.

In the inhibition assays relying on the wild type PAO1 reporter strain, quite different behaviors for the tested analogs were observed. The strongest inhibitors of luminescence appeared to be itc-13 and hal-12-Br, followed by itc-12, itc-11 and 4-Br-PHL (FIG. 6a,b; $IC_{50}$s: itc-13: 45.2±0.7 micro-M, hal-12-Br: 100±7 micro-M; itc-12, 113±19 micro-M; itc-11: ~300 micro-M). Strikingly, 4-Br-PHL displayed much weaker LasR antagonism ($IC_{50}$: ~250 micro-M) in the wild-type PAO1 reporter strain than in the *E. coli* reporter.

Figure 7:
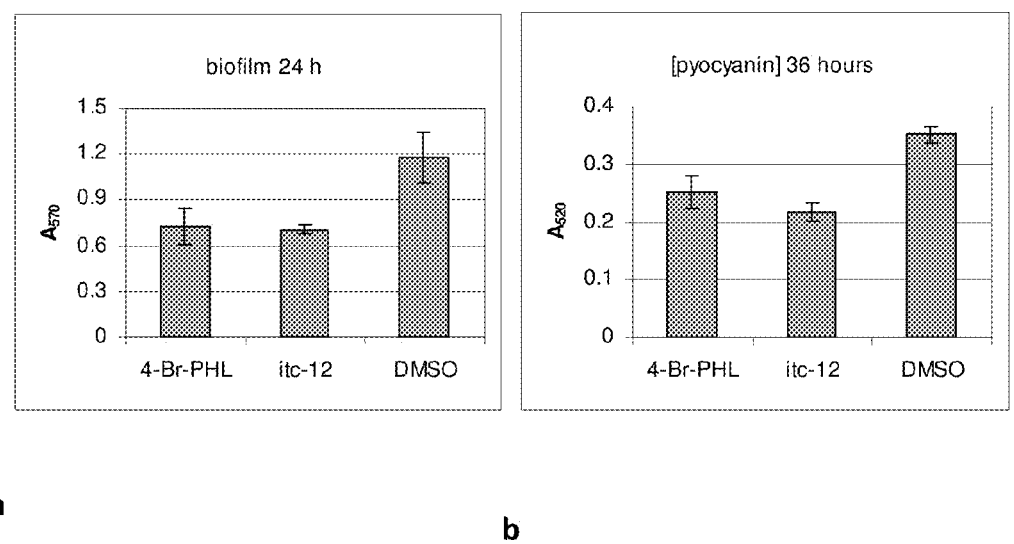
FIG. 7 Inhibition of biofilm formation (a) after 24 hours and pyocyanin production (b) after 36 hours, upon incubation of wild type *P. aeruginosa* strain PAO1 with 50 μM 4-Br-PHL, itc-12 or DMSO. Each bar represents the average of three experiments±SD.

In addition to studies relying on the *E. coli* reporter strain, experiments were performed using a PAO1 mutant that does not produce 3-oxo-$C_{12}$-HSL (i.e. strain PAO-JP2) to verify whether the various inhibitors showed specific 3-oxo-$C_{12}$-HSL antagonist activity (FIG. 7a,b). Of the nine probes considered, itc-13 ($IC_{50}$: 30±7 micro-M), hal-12-Cl (70±27 micro-M), hal-12-Br (85±1 micro-M), itc-12 (134±6 micro-M) and 4-Br-PHL (~200 micro-M) displayed significant antagonism. In case the mode of active inhibition was non-covalent, experiments were performed with an azido isostere analog of itc-12 (azido-C12) unable to react with Cys79. The inhibitory activity of this analog was significantly lower than that of itc-12 (data not shown), with no covalently labeled product being observed in MS measurements of purified LasR-LBD expressed in the presence of azido-C12 (data not shown).

It was also considered whether the inhibitory effects of the covalent QS inhibitors could be attributed to partial agonism, since several of the inhibitors (in particular, the isothiocyanates) showed agonism using the PAO-JP2-based reporter (FIG. 7c), albeit to markedly reduced levels, as compared to the natural autoinducer. The next experiments used itc-12 since this probe consistently displayed strong activity in all assays. When compared to the other inhibitors, itc-12 appeared to induce the expression of larger amounts of soluble LasR-LBD. Blackwell and co-workers recently showed that several of their inhibitors displayed characteristic partial agonism patterns[27]. Our data also display partial agonism patterns (FIG. 7d), although at high concentrations of itc-12, marked differences in the effects elicited by these other inhibitors and itc-12 was noted. Without wishing to be limited by a single hypothesis, it is possible that the observed differences can be explained by the covalent binding mode of the reactive itc-12 probe.

Isothiocyanate-Based Probes Inhibit QS-Regulated Activities

To assess whether the reactive probes inhibit QS-regulated activities, such as biofilm formation and pyocyanin production, the wild type *P. aeruginosa* PAO1 strain was incubated in the presence of itc-12 and 4-Br-PHL (both at 50 micro-M), or DMSO, as a control, in microtiter plates that allow analysis of 24 h biofilm formation and in vials allowing measurement of 36 h pyocyanin production. As shown in FIG. 8a,b, both activities were significantly inhibited in the presence of the isothiocyanate probe, as well as the known QS inhibitor, 4-Br-PHL. Full inhibition of either phenotype is rarely seen, suggesting regulation by QS-associated mechanisms to be only partial. However, even a partial reduction in biofilm formation may be sufficient to render the bacteria vulnerable to host responses, as not only is total biofilm mass affected upon disruption of QS, but also is its architecture, its degree of porosity and its extent of flexibility and robustness.

Discussion

With a set of compounds according to at least some embodiments of the present invention, it was possible to target the *P. aeruginosa* QS regulator, LasR, and examine whether QS can be inhibited through covalent binding of this protein. It was determined that the isothiocyanate-based probes covalently and selectively bound Cys79, found in the LasR binding pocket. Furthermore, through the use of several well-characterized reporter strains, it was possible to evaluate the influence of the nine synthetic inhibitors on *P. aeruginosa* quorum sensing-related gene expression. Although differences in measured activity between reporter assays were noted, strong inhibition of QS was observed for the isothiocyanate analogs.

Ambiguous effects were seen for the haloacetamides, with bromoacetamide hal-12-Br showing strong activity. No covalent interactions between any of the haloacetamides and LasR were, however, observed. From these results, it is possible that no covalent reaction had taken place between the haloacetamides and LasR, meaning that their inhibitory effect may be mediated in a manner similar to other strong inhibitors, namely via binding nascent LasR followed by protein misfolding and precipitation. When compared to 4-Br-PHL, the isothiocyanates showed similar activity overall, with low micromolar $IC_{50}$ values being measured for itc-12 and itc-13 in assays using the *E. coli* reporter strain. Perhaps most striking is the large difference in activity between itc-13 and 4-Br-PHL in the PAO-JP2-based antagonist assay. It should be noted though that comparison of $IC_{50}$ values of different compounds obtained through the use of different strains and reporter assays is, however, problematic, as differences in membrane composition, secondary regulation of gene expression, competing ligands, etc., may all have large effects on the observed inhibition. Therefore, it is difficult to draw absolute conclusions with respect to the extent of inhibition of specific QS systems by certain compounds. Nevertheless, a compound that shows good and specific inhibition in a reporter assay, as well as phenotypical inhibition in a wild type strain, can be regarded as a good candidate for further QS inhibition and mechanistic studies. The isothiocyanates showed significant inhibition of QS at low concentrations in all assays. As such, it was decided to study the efficacy and mode of action of one such compound, itc-12, in more detail. In assays with the wild type PAO1 strain, itc-12 showed significant inhibition of QS-controlled virulence factor expression, as well as biofilm formation.

Due to increasing bacterial resistance to new antibiotics, inhibition of bacterial virulence has been proposed as a viable new therapeutic target. Such a strategy may yield desired results without inducing resistance to drugs targeting virulence—in contrast to drugs targeting bacterial growth. Furthermore, covalent probes that target LasR (or its homologs in other bacteria, as well as structurally characterized receptors for other classes of QS molecules) may be used as molecular tools to provide novel insight into the mechanisms of activation and deactivation of bacterial quorum sensing.

Example 3

Synthesis of Disufide-Bond Containing Compounds

This non-limiting Example relates to the synthesis of a compound containing a disulfide bond according to at least some embodiments of the present invention, including the compound of Structure-C. The General Synthesis is as for Example 1 above. A non-limiting specific example of a synthetic procedure is given as follows.

10-Mercaptodecanoic Acid

A mixture of thiourea (282 mg, 3.54 mmol, 1.5 equiv), and 10-bromodecanoic acid (641 mg, 2.4 mmol) was refluxed in EtOH (5 mL) for 20 h. The solvent was removed in vacuo and 7.5 M NaOH (aq) (5 mL, 1.4 g, 3.54 mmol, 1.5 equiv) was added. The mixture was stirred for an additional 16 h at 90° C., under nitrogen. It was then cooled on an ice bath and 2M $H_2SO_4$ was added slowly under stirring. The organic product was extracted with $CH_2Cl_2$ (2×50 mL), dried with MgSO4, and evaporated in vacuo. Purification of the crude oil via flash chromatography ($CH_2Cl_2$:$^i$PrOH=99:1) gave the intermediate thiol as a white solid (398 mg, 81% yield: $^1$H NMR (CDCl3, 200 MHz) δ 1.29-1.40 (m, 10H), 1.53-1.66 (m, 4H), 2.34 (t, 7.6 Hz, 2H), 2.51 (q, 7.4 Hz, 2H).

10,10'-Disulfanediylbis(Decanoic Acid)

10-mercaptodecanoic acid (122 mg, 0.56 mmol) was dropped in a solution of NaOH (24 mg, 0.6 mmol), and KI (29.8 mg, 0.18 mmol) in 4 mL of $H_2O$:DMF (1:1). $I_2$ (75.8 mg, 0.29 mmol) was added portionwise until the yellow color persisted, and then $Na_2SO_3$ was added until a complete decoloring of the solution occurred. The resulting suspension was acidified with HCl (1N), and the aqueous phase was extracted with $CHCl_3$ (4×20 mL). The organic phase was washed with brine, dried over $MgSO_4$, and the solvent was evaporated in vacuo. The intermediate disulphide compound was obtained as a white solid in quantitative yield. $^1$H NMR (CDCl3, 400 MHz) δ 1.25-1.40 (m, 10H), 1.55-1.70 (m, 4H), 2.33 (t, 6.4 Hz, 2H), 2.66 (t, 7.4 Hz, 2H).

12,12'-Disulfanediylbis(3-Oxo-N-(2-Oxotetrahydrofuran-3-yl)Dodecanamide)

N-(dimethylamino)pyridine (DMAP) (77 mg, 0.62 mmol), N,N-dicyclohexylcarbodiimide (DCC) (136 mg, 0.65 mmol), dicarboxylic acid (121 mg, 0.3 mmol) and Meldrum's acid (85 mg, 0.6 mmol) were dissolved in 6 mL of dichloromethane. The resulting solution was stirred overnight and then filtered to remove N,N-dicyclohexyl urea formed in the reaction. The filtrate was concentrated in vacuo. The resulting residue was dissolved in DMF (5 mL) and α-amino-γ-butyrolactone hydrobromide (109 mg, 0.6 mmol) was added. The mixture was stirred at room temperature for 1 hour and at 60° C. for 4 additional hours. The resulting solution was diluted with ethyl acetate 30 mL, and washed with saturated sodium bicarbonate solution, 1 M sodium hydrogen sulfate solution and brine. The organic phase was dried over magnesium sulfate, filtered and concentrated in vacuo. Further purification was done by flash chromatography. (Yield 33%). MS (ESI) m/z: calcd: [M+H$^+$] 657.32, measured: [M+H$^+$] 657.22.

Example 4

Synthesis of Thiol Containing Compounds

This non-limiting Example relates to the synthesis of thiol-containing compounds, including the compound of Structure-D (also referred to herein as "thiol-11").

Figure 8:
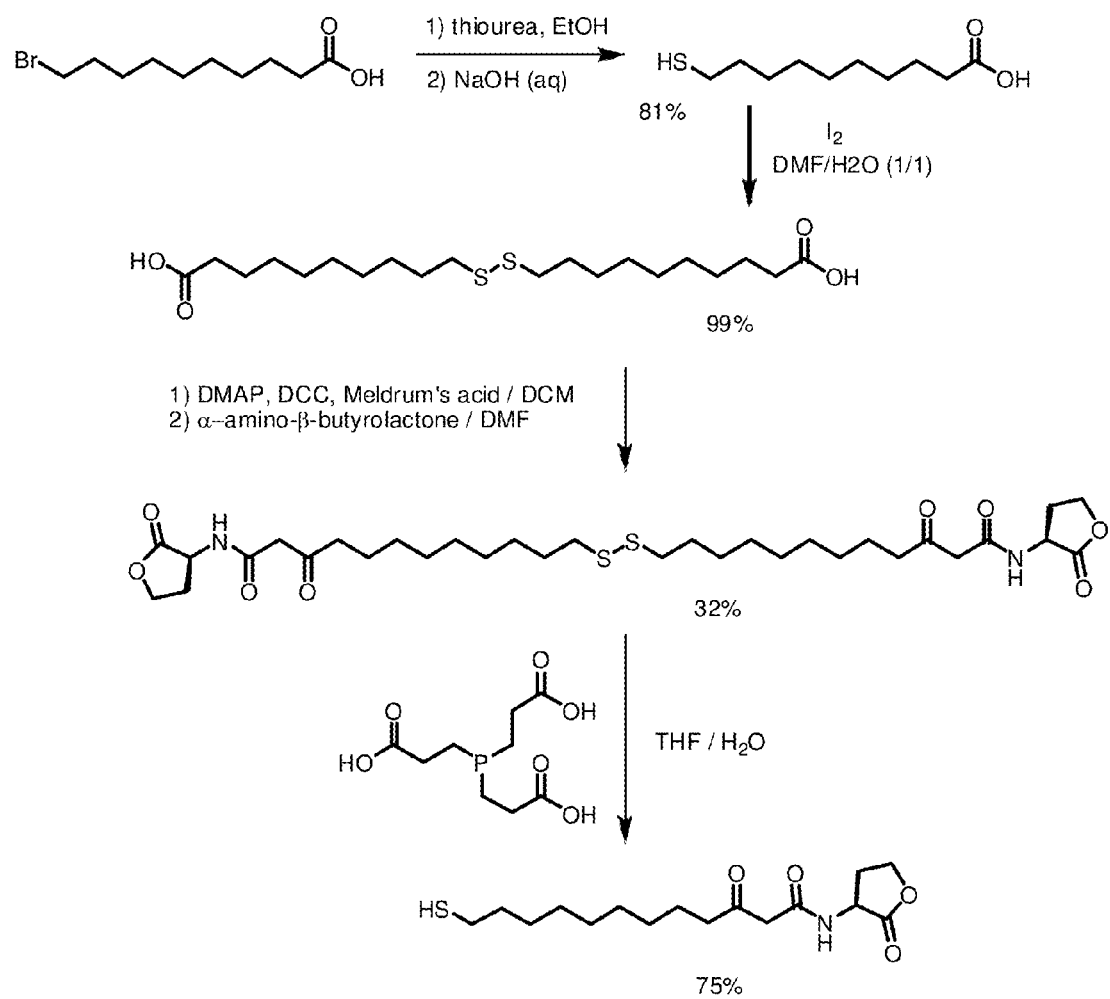
FIG. 8 shows the synthetic procedure for thiol-containing compounds, including the compound of Structure-D (also referred to herein as "thiol-11").

The General Synthesis is as for Example 1 above. The synthetic procedure is shown in FIG. 8. A non-limiting specific example of a synthetic procedure is given as follows, starting with the final compound of Example 3 (for example, Structure-C).

12-Mercapto-3-Oxo-N-(2-Oxotetrahydrofuran-3-yl) Dodecanamide

Dimer of 12-mercapto-3-oxo-N-(2-oxotetrahydrofuran-3-yl)dodecanamide (29 mg, 0.04 mmol) was dissolved in 0.5 mL of THF, and tris(2-carboxyethyl)phosphine hydrochloride (50 mg, 0.17 mmol) in water (0.5 mL) was added. The mixture was stirred under nitrogen overnight, diluted with 5 mL of water, and extracted with Et$_2$O (2×5 mL). The organic phase was washed with brine, dried with MgSO$_4$, filtered, concentrated and purified via flash chromatography to yield the desired compound as a white solid (70% Yield). MS (ESI) m/z: calcd: [M+H$^+$] 330.17, measured: [M+H$^+$] 330.06.

A similar process was followed to produce molecules in which the carbon chain was one carbon shorter and one carbon longer, with the only change being that the starting material was not 10-bromodecanoic acid (as described in Example 3) but rather 9-bromononanoic acid or 11-bromoundecanoic acid, respectively.

Example 5

Inhibition of Bacterial Communication by Thiol-11 and Itc-12

Figure 9:
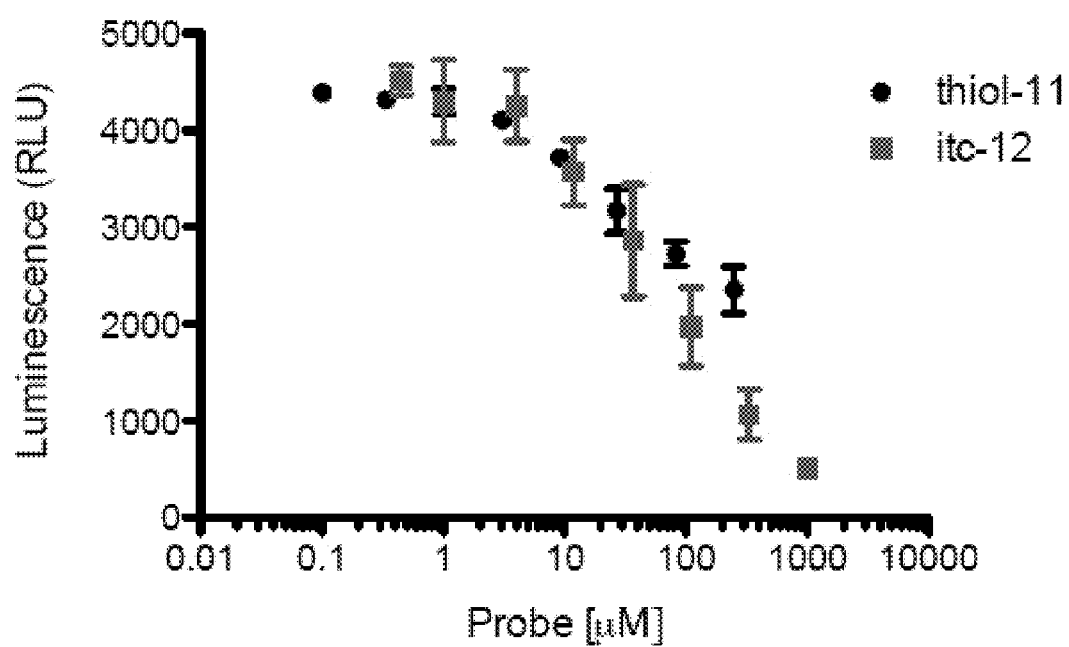
FIG. 9 shows that both thiol-11 and itc-12 inhibit virulence of *P. aeruginosa* in a dose-dependent manner.

The thiol-11 compound of Example 4 was tested with itc-12, a compound of Formula I (shown above), in the above described system for examining inhibition of lasI expression in PAO1-luxCDABE. As shown in FIG. 9, both thiol-11 and itc-12 inhibit virulence of *P. aeruginosa* in a dose-dependent manner, thereby demonstrating the specificity of these compounds.

Example 6

Use of Compounds for Anti-Biofilm Compositions

In at least some embodiments, compounds according to at least some embodiments of the present invention may optionally be used in an anti-biofilm composition for inhibiting or reducing biofilm formation.

Such a composition may optionally include a compound according to at least some embodiments of the present invention in a suitable carrier. The composition of the present disclosure can optionally contain additional components, e.g., dyes, antimicrobial agents, growth factors, anti-inflammatory agents, and the like (without wishing to provide a closed list). The term "antimicrobial agent" as used in the present disclosure includes antibiotics, antiseptics, disinfectants and combinations thereof. In embodiments, the antimicrobial agent may be an antiseptic, such as triclosan.

Classes of antibiotics that can be used in the composition include tetracyclines like minocycline; rifamycins like rifampin; macrolides like erythromycin; penicillins like nafcillin; cephalosporins like cefazolin; beta-lactam antibiotics like imipenem and aztreonam; aminoglycosides like gentamicin and TOBRAMYCIN®™; chloramphenicol; sulfonamides like sulfamethoxazole; glycopeptides like vancomycin; quinolones like ciprofloxacin; fusidic acid; trimethoprim; metronidazole; clindamycin; mupirocin; polyenes like amphotericin B; azoles like fluconazole; and beta-lactam inhibitors like sulbactam.

In other embodiments, silver salts, including silver salts of ionic furanones, may be added for their antimicrobial properties.

Examples of antiseptics and disinfectants which may be utilized in the compositions include but are not limited to hexachlorophene; cationic biguanides like chlorhexidine and cyclohexidine; iodine and iodophores like povidone-iodine; halo-substituted phenolic compounds like PCMX (i.e., p-chloro-m-xylenol) and triclosan (i.e., 2,4,4'-trichloro-2' hydroxy-diphenylether); furan medical preparations like nitrofurantoin and nitrofurazone; methenamine; aldehydes like glutaraldehyde and formaldehyde; and alcohols. In some embodiments, at least one of the antimicrobial agents may be an antiseptic, such as triclosan.

The antimicrobial compositions of the present disclosure may contain various optional ingredients, such as stabilizing agents, thickeners, colors, and the like. The optional ingredients may be present in an amount of up to about 10% of the total weight of the antimicrobial composition.

Example 7

Use of Compounds for Medical Devices

In at least some embodiments, compounds according to at least some embodiments of the present invention may optionally be used to treat medical devices for inhibiting biofilm formation. Medical devices may optionally be formed of absorbable materials, nonabsorbable materials, and combinations thereof. Suitable absorbable materials which may be utilized to form the medical device include trimethylene carbonate, caprolactone, dioxanone, glycolic acid, lactic acid, glycolide, lactide, homopolymers thereof, copolymers thereof, and combinations thereof, in which the compound is optionally absorbed into or formed with the material. Suitable non-absorbable materials which may be utilized to form the medical device include polyolefins, such as polyethylene, polypropylene, copolymers of polyethylene and polypropylene, and blends of polyethylene and polypropylene, in which the compound is optionally coated onto the device. Of course any other suitable polymer may optionally be used for the medical device.

If a compound of the present invention is applied to the medical device with a coating, any polymer suitable for use in the coating may be utilized in accordance with the present disclosure. Polymers may be bioabsorbable or nonabsorbable. In at least some embodiments, a bioabsorbable film-forming polymer may be utilized in a device and/or coating of the present disclosure. Film-forming polymers which may be utilized in the coating are within the purview of those skilled in the art and include those containing linkages derived from monomers including, for example, glycolide, lactide, glycolic acid, lactic acid, caprolactone, trimethylene carbonate, dioxanones, dioxepanones, and the like, and homopolymers, copolymers and combinations thereof.

REFERENCES

1. Kaper, J. B. & Sperandio, V. Bacterial cell-to-cell signaling in the gastrointestinal tract. Infect Immun 73, 3197-209 (2005)
2. Winzer, K., Hardie, K. R. & Williams, P. Bacterial cell-to-cell communication: sorry, can't talk now—gone to lunch! Curr Opin Microbiol 5, 216-22 (2002.(
3. Taga, M. E. & Bassler, B. L. Chemical communication among bacteria. Proceedings of the National Academy of Sciences of the United States of America 100, 14549-14554 (2003.(
4. Lyon, G. J. & Muir, T. W. Chemical signaling among bacteria and its inhibition. Chemistry & Biology 10, 1007-1021 (2003.(
5. Kelly, D., Conway, S. & Aminov, R. Commensal gut bacteria: mechanisms of immune modulation. Trends Immunol 26, 326-33 (2005.(
6. Auger, S., Krin, E., Aymerich, S. & Gohar, M. Autoinducer 2 affects biofilm formation by Bacillus cereus. Appl Environ Microbiol 72, 937-41 (2006.(
7. Stoodley, P., Sauer, K., Davies, D. G. & Costerton, J. W. Biofilms as complex differentiated communities. Annual Review of Microbiology 56, 187-209 (2002.(
8. Latifi, A., Foglino, M., Tanaka, K., Williams, P. & Lazdunski, A. A hierarchical quorum-sensing cascade in Pseudomonas aeruginosa links the transcriptional activators LasR and RhIR (VsmR) to expression of the stationary-phase sigma factor RpoS. Mol Microbiol 21, 1137-46 (1996.(
9. Pesci, E. C., Pearson, J. P., Seed, P. C. & Iglewski, B. H. Regulation of las and rhl quorum sensing in Pseudomonas aeruginosa. J Bacteriol 179, 3127-32 (1997.(
10. Lequette, Y., Lee, J. H., Ledgham, F., Lazdunski, A. & Greenberg, E. P. A distinct QscR regulon in the Pseudomonas aeruginosa quorum-sensing circuit. J Bacteriol 188, 3365-70 (2006.(
11. Bottomley, M. J., Muraglia, E., Bazzo, R. & Carfi, A. Molecular insights into quorum sensing in the human pathogen Pseudomonas aeruginosa from the structure of the virulence regulator LasR bound to its autoinducer. J Biol Chem 282, 13592-600 (2007.( It will be appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination. It will also be appreciated by persons skilled in the art that the present invention is not limited by what has been particularly shown and described hereinabove. Rather the scope of the invention is defined only by the claims which follow.

What is claimed is:

1. A compound of formula I:

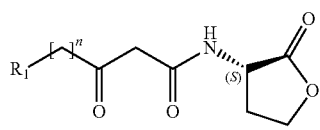

in which n represents the number of carbons and n=1-18, and $R_1$ is selected from the group consisting of O=C=N—, S=C=N—, and Se=C=N—.

2. A composition comprising the compound of claim 1 in a suitable carrier.

3. The composition of claim 2, further comprising one or more of dyes, antimicrobial agents, growth factors, or anti-inflammatory agents.

4. The composition of claim 3, further comprising an additional excipient.

5. The compound of claim 1, wherein $R_1$ is S=C=N— and n is an integer selected from the group consisting of 8, 9, or 10.

6. The compound of claim 5, wherein the compound is

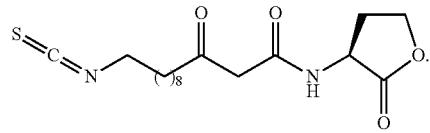

* * * * *